(12) United States Patent
Lohbihler

(10) Patent No.: US 9,024,810 B2
(45) Date of Patent: May 5, 2015

(54) METHOD AND APPARATUS FOR RANGING FINDING, ORIENTING, AND/OR POSITIONING OF SINGLE AND/OR MULTIPLE DEVICES

(75) Inventor: Andrew H. Lohbihler, Waterloo (CA)

(73) Assignee: XYZ Interactive Technologies Inc. (CA)

( * ) Notice: Subject to any disclaimer, the term of this patent is extended or adjusted under 35 U.S.C. 154(b) by 854 days.

(21) Appl. No.: 13/189,878

(22) Filed: Jul. 25, 2011

(65) Prior Publication Data

US 2011/0279366 A1 Nov. 17, 2011

Related U.S. Application Data

(63) Continuation-in-part of application No. PCT/CA2010/000095, filed on Jan. 27, 2010.

(60) Provisional application No. 61/147,711, filed on Jan. 27, 2009, provisional application No. 61/367,787, filed on Jul. 26, 2010, provisional application No. 61/369,994, filed on Aug. 2, 2010, provisional application No. 61/371,053, filed on Aug. 5, 2010.

(51) Int. Cl.
*G01S 11/06* (2006.01)
*G01S 11/12* (2006.01)
(Continued)

(52) U.S. Cl.
CPC .................. *G01S 11/06* (2013.01); *G01S 11/12* (2013.01); *G01S 11/14* (2013.01); *G01S 5/0247* (2013.01); *G01S 5/163* (2013.01); *G01S 5/186* (2013.01); *G06F 3/0325* (2013.01); *G06F 3/0346* (2013.01)

(58) Field of Classification Search
CPC ....... G06F 3/0346; G01S 11/02; G01S 5/186; G01S 5/163; G01S 5/0247; G01S 11/06; G01S 11/14; G01S 11/12

USPC .......................................... 342/134; 356/4.07
See application file for complete search history.

(56) References Cited

U.S. PATENT DOCUMENTS 3,898,383 A  8/1975  Herbits
3,918,297 A * 11/1975 Rocha ............................ 73/607

(Continued)

FOREIGN PATENT DOCUMENTS

CN  87105803 A  6/1988
CN  1241379     2/2006

(Continued)

OTHER PUBLICATIONS

Int'l Search Report & Written Opinion issued in PCT/CA2010/000095 (2010).

(Continued)

*Primary Examiner* — Matthew M Barker
(74) *Attorney, Agent, or Firm* — Katten Muchin Rosenman LLP

(57) ABSTRACT

A method and apparatus for ranging finding of signal transmitting devices is provided. The method of signal reception is digitally based only and does not require receivers that are analog measurement devices. Ranging can be achieved using a single pulse emitting device operating in range spaced relation with a minimum of a single signal transmitter and a single digital receiver and processing circuitry. In general a plurality of transmitting pulsed emitters may be ranged and positioned virtually simultaneously in 3-dimensions (XYZ coordinates) using a configuration of a plurality of digital receivers arranged in any fixed 3-dimensional configuration. Applications may involve at least one single transmitter to receiver design to determine range, or at least one transmitted reflecting signal off from an object to determine range.

25 Claims, 17 Drawing Sheets

(51) Int. Cl.
  *G01S 11/14* (2006.01)
  *G01S 5/02* (2010.01)
  *G01S 5/16* (2006.01)
  *G01S 5/18* (2006.01)
  *G06F 3/0346* (2013.01)
  *G06F 3/03* (2006.01)

(56) References Cited

U.S. PATENT DOCUMENTS

| | | | |
|---|---|---|---|
| 4,458,340 A * | 7/1984 | Lautzenhiser | 367/32 |
| 4,740,792 A | 4/1988 | Sagey et al. | |
| 4,851,661 A | 7/1989 | Everett, Jr. | |
| 4,866,526 A * | 9/1989 | Ams et al. | 348/69 |
| 4,924,109 A | 5/1990 | Weber | |
| 5,594,238 A | 1/1997 | Endruschat | |
| 5,640,151 A | 6/1997 | Reis et al. | |
| 5,712,558 A | 1/1998 | Saint-Cyr | |
| 5,977,878 A | 11/1999 | Lang | |
| 5,977,882 A | 11/1999 | Moore | |
| 6,107,938 A | 8/2000 | Du | |
| D435,473 S | 12/2000 | Eckel | |
| 6,163,275 A | 12/2000 | Hartzell | |
| 6,369,517 B2 | 4/2002 | Song | |
| 6,821,211 B2 | 11/2004 | Otten | |
| 7,038,589 B2 | 5/2006 | Schmidt et al. | |
| 7,084,860 B1 | 8/2006 | Jaeger et al. | |
| 7,115,856 B2 | 10/2006 | Peng | |
| 7,116,056 B2 | 10/2006 | Jacoby, Jr. | |
| 7,423,576 B2 | 9/2008 | Sahinoglu et al. | |
| 7,512,505 B2 | 3/2009 | Harles | |
| 7,518,738 B2 | 4/2009 | Cavallucci | |
| 7,653,883 B2 | 1/2010 | Hotelling et al. | |
| 7,656,308 B2 | 2/2010 | Atkins | |
| 7,852,318 B2 | 12/2010 | Altman | |
| 7,973,589 B2 | 7/2011 | Rothenberger | |
| 8,217,482 B2 | 7/2012 | Basoor | |
| 8,294,576 B2 | 10/2012 | Matsuoka | |
| 8,363,894 B2 | 1/2013 | Gerber | |
| 8,507,863 B2 | 8/2013 | Holenarsipur | |
| 2001/0055353 A1 | 12/2001 | Rybicki et al. | |
| 2004/0056849 A1 | 3/2004 | Lohbihler et al. | |
| 2004/0127304 A1 | 7/2004 | Plank, Jr. | |
| 2004/0186623 A1 | 9/2004 | Dooley et al. | |
| 2006/0166681 A1 | 7/2006 | Lohbihler | |
| 2007/0193582 A1 | 8/2007 | Kwok | |
| 2008/0029316 A1 | 2/2008 | Jaeger et al. | |
| 2008/0042993 A1 | 2/2008 | Jaeger et al. | |
| 2008/0084271 A1 | 4/2008 | Jaeger et al. | |
| 2008/0192025 A1 | 8/2008 | Jaeger et al. | |
| 2008/0279287 A1 | 11/2008 | Asahina | |
| 2008/0316085 A1 | 12/2008 | Rofougaran et al. | |
| 2008/0316104 A1 | 12/2008 | Seong et al. | |
| 2011/0121181 A1 | 5/2011 | Costello | |
| 2013/0214166 A1 | 8/2013 | Barlow | |
| 2013/0300316 A1 | 11/2013 | Engel-Hall | |

FOREIGN PATENT DOCUMENTS

| | | |
|---|---|---|
| CN | 1997959 A | 7/2007 |
| EP | 0392152 A2 | 10/1990 |
| EP | 1178454 B1 | 2/2002 |
| EP | 1552988 A3 | 7/2005 |
| JP | H04/280127 | 10/1992 |
| JP | H07/294617 | 11/1995 |
| JP | H09/133747 | 5/1997 |
| JP | H09/292454 | 11/1997 |
| JP | 2000/111641 | 4/2000 |
| JP | 2002/168934 | 6/2002 |
| JP | 2002/365364 | 12/2002 |
| JP | 2004534212 | 11/2004 |
| JP | 2004536634 | 12/2004 |
| JP | 2004536715 | 12/2004 |
| JP | 2005/503219 | 1/2006 |
| JP | 2006/112475 | 4/2006 |
| JP | 200826310 | 2/2008 |
| JP | 2009516935 | 4/2009 |
| JP | 2009/168657 | 7/2009 |
| WO | 02/095518 A2 | 11/2002 |
| WO | WO 2004/015555 | 2/2004 |
| WO | WO/2006/030422 | 3/2006 |
| WO | 2006056814 A1 | 6/2006 |
| WO | 2007/060749 A1 | 5/2007 |
| WO | 2007/067008 A1 | 6/2007 |
| WO | WO 2007/067008 | 6/2007 |

OTHER PUBLICATIONS

First Office Action, Japan Patent Office, Application 2011-546553, Feb. 4, 2014.
Extended Search Report, European Patent Office, Application 10735452.4, Feb. 19, 2014.
First Office Action, Chinese Patent Office, Application 201080014777.3, Jan. 22, 2013.
Second Office Action, Chinese Patent Office, Application 201080014777.3, Sep. 11, 2013.
Notice to Grant, Chinese Patent Office, Application 201080014777.3, Feb. 26, 2014.
Second Office Action, Japan Patent Office, Application 2011-546553, Sep. 8, 2014.
Ryu et al., T-Less: A Novel Touchless Human-Machine Interface Based on Infrared Proximity Sensing, 2010, IEEE/RSJ International Conference on Intelligent Robots and Systems, Mar. 12, 2010.

* cited by examiner

METHOD AND APPARATUS FOR RANGING FINDING, ORIENTING, AND/OR POSITIONING OF SINGLE AND/OR MULTIPLE DEVICES

CROSS REFERENCE TO RELATED APPLICATIONS

The present application is a Continuation-in-Part of copending international patent application no. PCT/CA2010/000095, filed Jan. 27, 2010 (entitled "A METHOD AND APPARATUS FOR RANGING FINDING, ORIENTING, AND POSITIONING OF SINGLE OR MULTIPLE DEVICES"), which claims priority under 35 U.S.C. §119(e) to U.S. Provisional Patent Application No. 61/147,711, filed Jan. 27, 2009 (entitled "A METHOD AND APPARATUS FOR RANGING FINDING, ORIENTING, AND POSITIONING OF SINGLE OR MULTIPLE DEVICES"); and the present application claims priority under 35 U.S.C. §119 (e) to U.S. Provisional Patent Application No. 61/367,787, filed Jul. 26, 2010 (entitled "A METHOD AND APPARATUS FOR RANGING FINDING, ORIENTING, AND POSITIONING OF SINGLE AND/OR MULTIPLE DEVICES"); U.S. Provisional Patent Application No. 61/369,994; filed Aug. 2, 2010 (entitled "A METHOD AND APPARATUS FOR RANGING FINDING, ORIENTING, AND POSITIONING OF SINGLE OR MULTIPLE DEVICES"); and U.S. Provisional Patent Application No. 61/371,053; filed Aug. 5, 2010 (entitled "A TOUCH-LESS TOGGLE/DIRECTIONAL LIGHT SWITCH AND DIMMER"). The disclosures set forth in the referenced applications are incorporated herein by reference in their entireties, including all information as originally submitted to the United States Patent and Trademark Office.

BACKGROUND

1. Field

The present disclosure relates to range finding of one or more signal transmitting devices, and hence to determining their orientation and position based on a transmitted signal therefrom.

2. Description of the Related Art

Current methods to locate electromagnetic waves in three-dimensions rely on intensity, wavelength, and phase measurements using planar sensor arrays combined with sensor image processing algorithms. In lower frequency systems, measurements taken by planar sensor arrays are correlated to find the 3D location of electromagnetic wave sources. By measuring the phase shift of waves between sensors, the position of the source can be triangulated or trilaterated. Higher frequency systems in the visible light and infrared range typically use imaging systems to determine the 3D location of sources. Other systems for 3D location use active EM beams with sensors that measure the reflected waves like Light Detecting and Ranging (LIDAR) or radar systems, and are intended for long-range use. The emergence of 3D gaming devices has increased the desire for 3D positioning in short range for a variety of gaming functions including 3D object rendering and control to allow for a realistic real-time gaming experience.

Current methods to locate radio frequency waves rely upon a form of triangulation, whether a single directional antenna system or a phased array radar system with multiple antennas and signal processing algorithms. A single antenna typically monitors signal amplitude to find the range of the radio frequency source, and two or more fixed antennas or a single rotating antenna to find the direction. There is usually no consistent approach to operate these systems over long range, nor is there a reliable method of processing ubiquitous radio signals in short range without the complexity of multi-path fading associated with reflecting waves from the surrounding environment. Attempts to use higher frequencies with coded modulations and lower signal power can reduce multipath effects but not enough to all for high resolution positioning of a radio transmitter source.

The current state of the art for sensing infrared sources in 3D employs imaging systems that take successive pictures of the surrounding area. These imaging systems are limited to a specific field of view (FOV) in a relatively short range and incorporate scanning algorithms and image processing for target tracking and identification. Such systems also require longer signal processing times depending on the resolution required and the number of imaging scanners involved, and hence are of limited use for real-time control applications. Complex image processing algorithms must be incorporated to determine the 3D position of an IR source to separate from ambient sources. Lensing systems are also subject to system focus, objects outside of the focus of the system will be obscured requiring a focus time to correct. The combination of a wide FOV, focus time, image processing algorithms, and multiple sensors creates a complex, high-cost system with many components to determine the 3D location of IR sources.

Light detecting and ranging (LIDAR) systems, or laser radar function by sending out pulses of light and processing the returned signals. By measuring the time of the photon flight, LIDAR systems spatially derive objects in the surrounding environment. Such systems also include a laser pulse at different frequencies, such that the relative signal strength of the returned wavelengths measure characteristics of the atmosphere such as gas composition, but not for ranging purposes. Unintended reflecting objects and changing gas properties will interfere with the ranging performance as they are intended mainly for long-range tracking applications. Time of flight tracking in the short range is not considered practical.

Lately, the emergence of 3D graphical games has increased a desire for 3D wireless devices allowing users to interface with games with built-in 3D features. There is also a need for faster rates of data for positioning in 3D, to allow users to have a more natural interaction with the computer, providing smoother positioning in a substantially delay-free manner. Also needed is a higher resolution positioning for increasingly sophisticated games and interfaces with high-resolution computer screens. However, there is an increasing need for devices that are truly wireless and allow multiple users to interface with the same interface screen and with a variety of controller functions. Gaming functions like user identity (for multi-user games), switching, pointing, 3D object control, and other 3D rendering functions for virtual reality.

Some wireless interface devices operate at longer ranges (for example, about one to three meters) from the computer screen and are based on infra-red and/or acoustic media to transmit signals that are used to locate the transmitter in 3D space. The signals are received by a base receiver that triangulates the position of the hand-held transmitting device based on time-delays. These devices are suitable for disabled users, and for users who require an interface over a wider volume of space such as for gaming. These technologies generally have limited range of operation and commonly require that a power cable be tethered to the hand-held device to provide power and be operable to switch signals between the handheld device and a base receiver. Accordingly, these devices are rather awkward to use as they are not fully wireless, or are intended to provide a 2D screen output and have no ability to do ranging.

Existing interface or gaming systems (like computer mice and joysticks) that display absolute or relative position introduce some kind of mechanical or data-link delay that lowers the presentation speed to any display or monitoring device. Accordingly, there is a need for systems and methods of sensing position in 2D and 3D that increase the rate at which absolute position data is presented on a display for multiple objects and icons viewed on a computer screen.

In the field of golf swing analysis many inventions have described using IR transmitters and receivers to begin a timing sequence of start of swing and end of swing. In particular the U.S. Pat. No. 6,821,211 describes a system where the objective is to measure a start and stop time hence the speed and angle of the golf club path, depending on the IR emitter and receiver configuration. The offset alignment and height of the club swing is described in U.S. Pat. No. 7,329,193 which describes an IR timing starter and the use of ultra-sonic pulses for ranging the club foot inside a swing sensing corridor. There is no embodiment in the prior-art that mentions use of the signal itself configured with a signal strength code that determines the range of the swinging club to the mat.

US Navy U.S. Pat. No. 4,851,661 discusses using power levels and thresholds for edge detection and angle offset measurement. This technique mentioned in prior art is crude but defines a simplistic method of using power levels set by multiple IR LED's being turned-on at different times, ultimately to detect and approaching robot, and for measuring the offset angle. This approach is not used for range measurement in any way.

DETAILED DESCRIPTION OF EXEMPLARY EMBODIMENTS

Several exemplary embodiments are provided, by way of examples only, with reference to the appended drawings, wherein.

Figure 10:
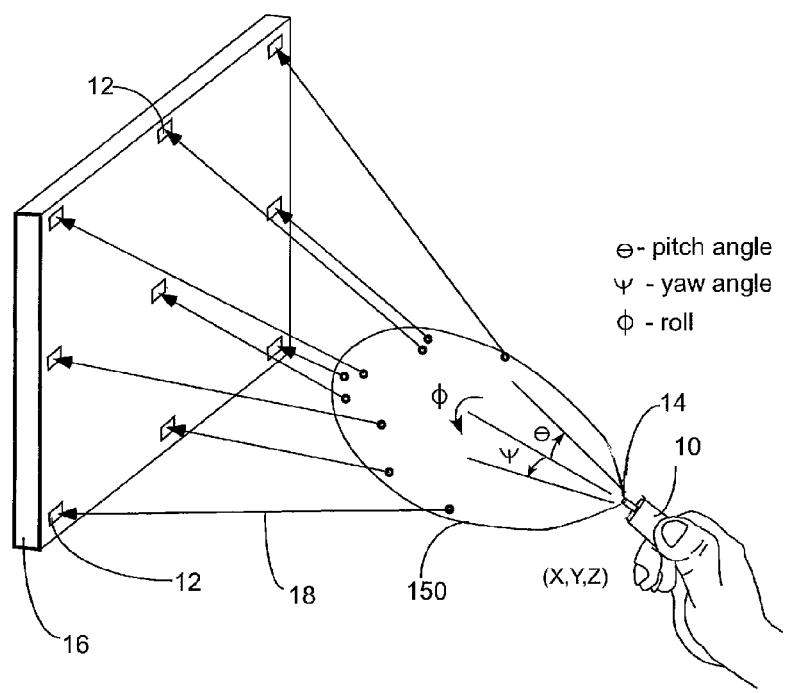
Figure 11:
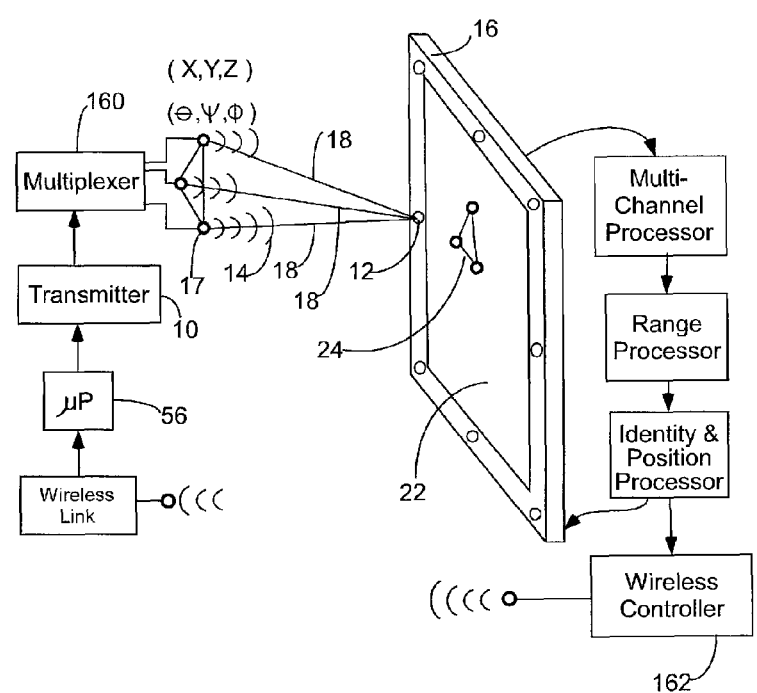
Figure 12A:
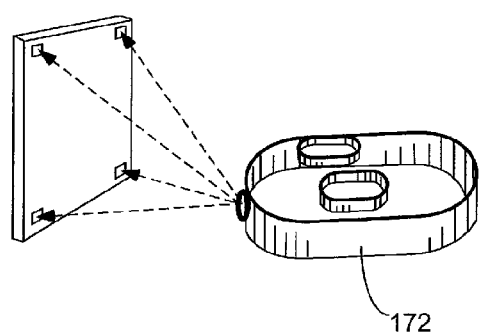
Figure 12B:
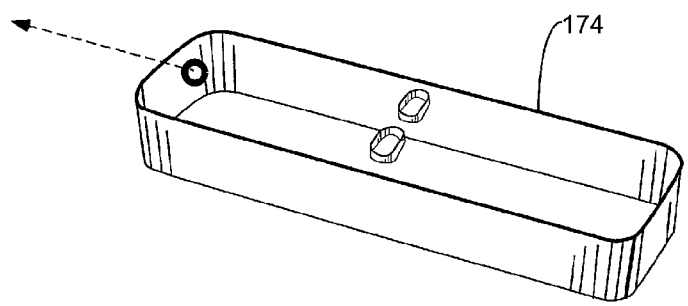
Figure 13:
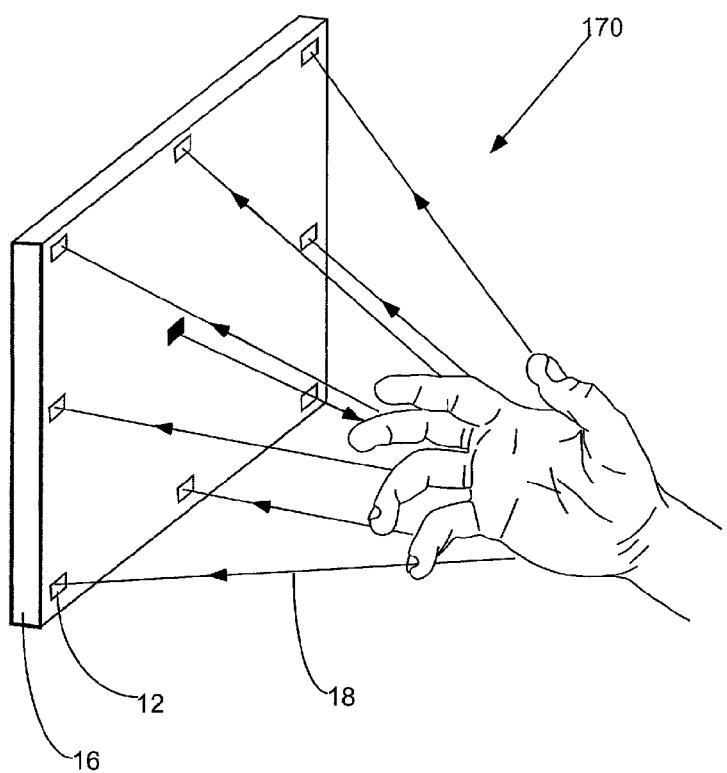
Figure 14:
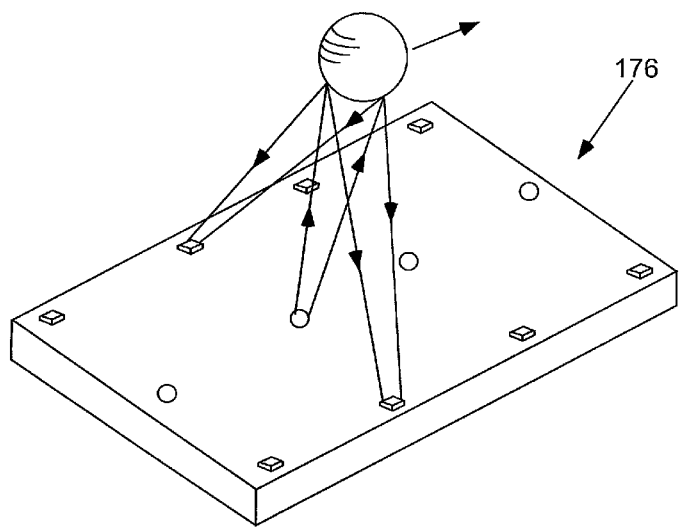
Figure 15:
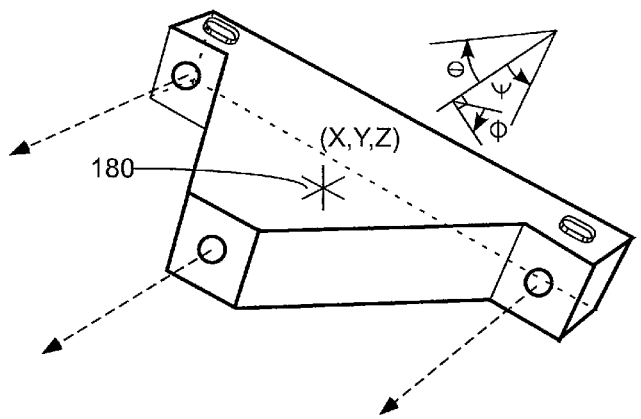
Figure 16:
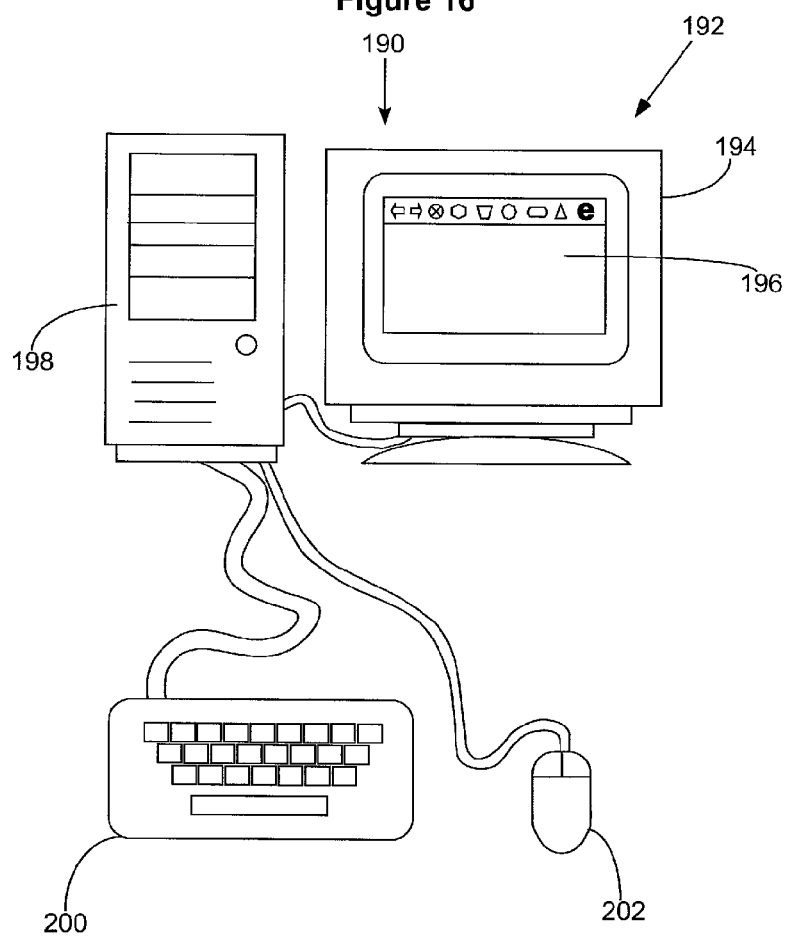
Figure 17:
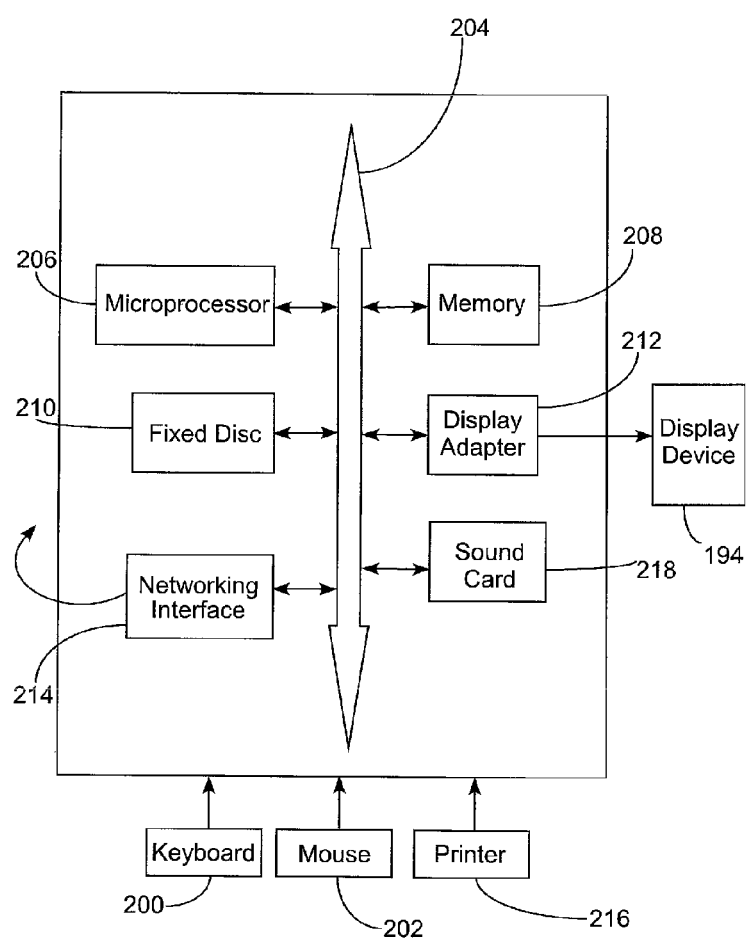

FIG. 10 a schematic view of an exemplary transmitter in another operable configuration with a receiver array;

FIG. 11 is another schematic view of exemplary transmitters in another operable configuration with a perimeter receiver array;

FIGS. 12a and 12b are perspective views of additional exemplary embodiments, in the form of a mouse and pointer;

FIG. 13 is a schematic view of exemplary transmitters in another operable configuration with an receiver array;

FIG. 14 is a perspective schematic view of still another exemplary embodiment, in this case of a golf mat;

FIG. 15 is a perspective schematic view of still another exemplary embodiment, in this case of a 6DOF controller; and FIGS. 16 and 17 are schematic views of a computer system in accordance with an exemplary embodiment herein.

It should be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical or electrical connections or couplings. Furthermore, and as described in subsequent paragraphs, the specific mechanical or electrical configurations illustrated in the drawings are intended to exemplify embodiments of the disclosure. However, other alternative mechanical or electrical configurations are possible which are considered to be within the teachings of the instant disclosure. Furthermore, unless otherwise indicated, the term "or" is to be considered inclusive. Further, the term "a" when followed by a single recitation of a named feature is to be construed inclusively, to mean that it includes within its meaning, more than one of the named feature, or more than one feature including the named feature.

Exemplary embodiments provide a system whereby a position of one or more transmitters can be determined by one or more receivers based on a signal from each transmitter, received by at least one of said receivers, each receiver being coupled to an electronic circuit and operable to determine a location of a particular transmitter based on a comparison between the signals received by the receivers.

A system for sensing a position of a transmitter uses a transmitter constructed to transmit a pulsed signal. The at least two receivers are located in a spaced relation relative to the transmitter and to each other. At least two receivers are each operable to receive a different version of the signal. An electronic circuit is coupled to the at least two receivers, and is operable to determine the position of the transmitter in relation to the at least two receivers based on a comparison between the different versions of the signal.

A method of determining a range of a transmitter, the transmitter being constructed to transmit a signal to at least one receiver in a spaced relation to the transmitter with an electronic circuit connected to the receiver, the method comprising operating the transmitter to transmit a radio signal to the receiver and determining a range of the transmitter from the radio signal that is received by the receiver.

Receivers comprise at least two receivers that are in a spaced relationship to one another and to a transmitter. The receivers are each operable to receive a different version of a signal transmitted by the transmitter. The receivers are connected to an electronic circuit, and the receivers are constructed in the circuit to determine a location of the transmitter in relation to the receivers based on a comparison between each different version of the signal.

A method for sensing a location of a transmitter uses at least two receivers that are spaced apart from one another and spaced apart from the transmitter. The transmitter operates to transmit a signal to the at least two receivers, each of the least two receivers being operable to receive a different version of the signal. The method comprises operating the transmitter to transmit a signal, operating the at least two receivers to each receive a different version of the signal and determining a location of the transmitter based on a comparison of the two versions of the signal.

A system for sensing position comprising at least two transmitters, each operable to transmit a unique signal. There are at least two receivers in a spaced relationship to each other, and each receiver is operable to receive a different version of each of the signals. The receivers are comprised of a wave energy input device, and a receiver element. An electronic circuit is coupled to the receiver element and is operable to substantially simultaneously determine a location of each of the radio transmitters in relation to the receivers by distinguishing the transmitters based on the unique data field, and based on a comparison between each different version of each respective signal.

A system for identifying and locating one or more transmitters in a transmitting area comprises a signal propagating medium for conducting signals throughout the transmitting area. At least one of the transmitters has means for producing a signal and coupling the signal to the signal propagating medium. The signal has a combined pulsed coding and signal strength coding, each signal including a unique code identifying a transmitter from which the signal is emitted. Receivers are associated with the transmitting area and are connected to the propagating to receive at least one signal from the at least one transmitter, with means for decoding the signal to identify and locate the at least one transmitter.

A system for sensing a location of a transmitter uses a transmitter constructed to emit a signal that is unique to the transmitter. A receiver is operable to receive the signal and to identify the transmitter based on the signal and pre-programmed information in the receiver. An electronic circuit is coupled to the receiver, the electronic circuit being operable to determine a location of the transmitter in relation to the receiver based on the signal.

A method for sensing a location of the reflected signal from a transmitter uses at least two receivers that are spaced apart from one another and spaced apart from the transmitter. The transmitter operates to transmit a signal to the object that reflects the transmitted signal to at least two receivers, each of the least two receivers being operable to receive a different version of the reflected signal. The method comprises operating the transmitter to transmit a signal, to a reflecting object and hence operating the at least two receivers to each receive a different version of the reflected signal and determining a location of the transmitter based on a comparison of the two versions of the signal.

As will be described, an exemplary embodiment provides a system including at least one signal transmitter 10 and at least one signal receiver 12 operable to receive the emitted signal 14. As will be discussed, the emitted signal 14 includes a single packet of information that identifies the transmitter identity, communicates the synchronizing timing of the packet, as well as including a train of pulses with varying pulse strength along the train. The signal receiver 12 upon receiving the signal, is operable to identify the transmitter 10 (in the case of two or more transmitters), synchronize the timing of the received pulse with other receivers 12 (in the case of two or more receivers), and to count the number of pulses received above a predetermined threshold. In this case the count represents the range between the transmitter 10 and receiver 12. Using calibration and a plurality of other receivers arranged or configured as an array 16, the range and location of the transmitter(s) may be individually and separately be calculated.

Figure 1:
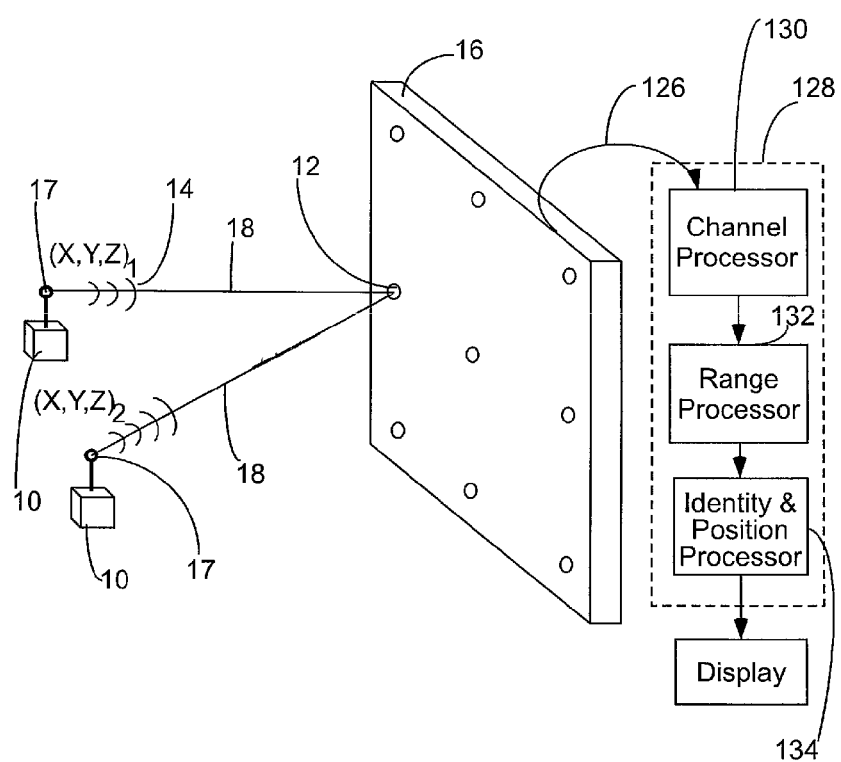
FIG. 1 is a schematic view of several exemplary transmitters in an operable configuration with a planar receiver array.

An exemplary embodiment is shown in FIG. 1 with one or more signal transmitters 10 (in this case two), sending signals 14 from an emitter 17 to one or more signal receivers 12 (in this case nine) that are affixed to the array 16. The array 4, in this case, is shown in a planar configuration, though the array 16 may be provided in other configurations as need be. The system is further operable to determine a range 18 between each of the signal receivers 12 and the corresponding signal transmitters 10, and may also, in some cases, determine the identity of each signal transmitter 10, its position, and/or angular orientation 20. Data resulting therefrom may be recorded in a computer or on a display unit 22, as 3-dimensional representable data or rendered as a 3D image or icon 24 (FIG. 2).

Figure 2:
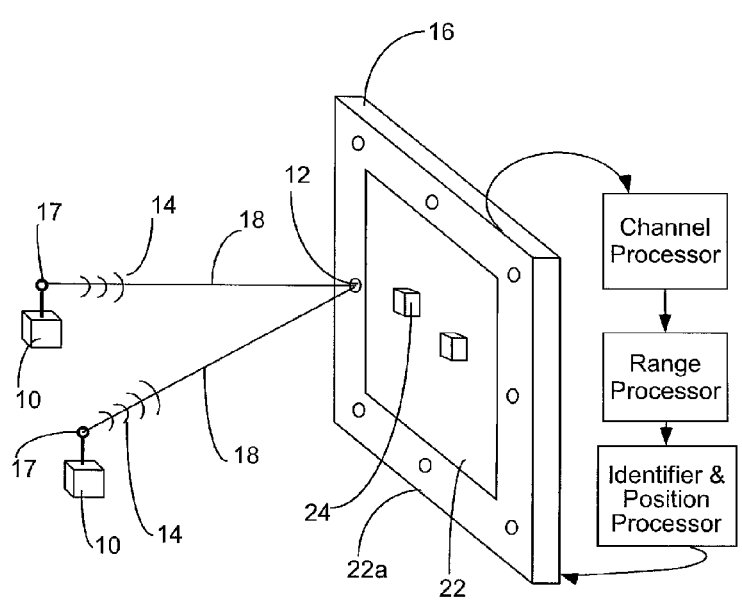
FIG. 2 is a schematic view of exemplary transmitters in another operable configuration with a perimeter receiver array.

An exemplary embodiment, as shown in FIG. 2, includes any number (in this case two) of signal transmitters 10 sending signals 14 to any number of signal receivers 12 (in this case eight) that are affixed to a perimeter 22a of the display unit 22 such that the corresponding icons 24 are displayed thereon, for example as a precise rendering of the real-time position and motion of the actual signal transmitters 10. Other positions or data representing images, position or range or the like may also be presented on the display unit 22, or for that matter other formats on other display or messaging devices as need be.

Figure 3:
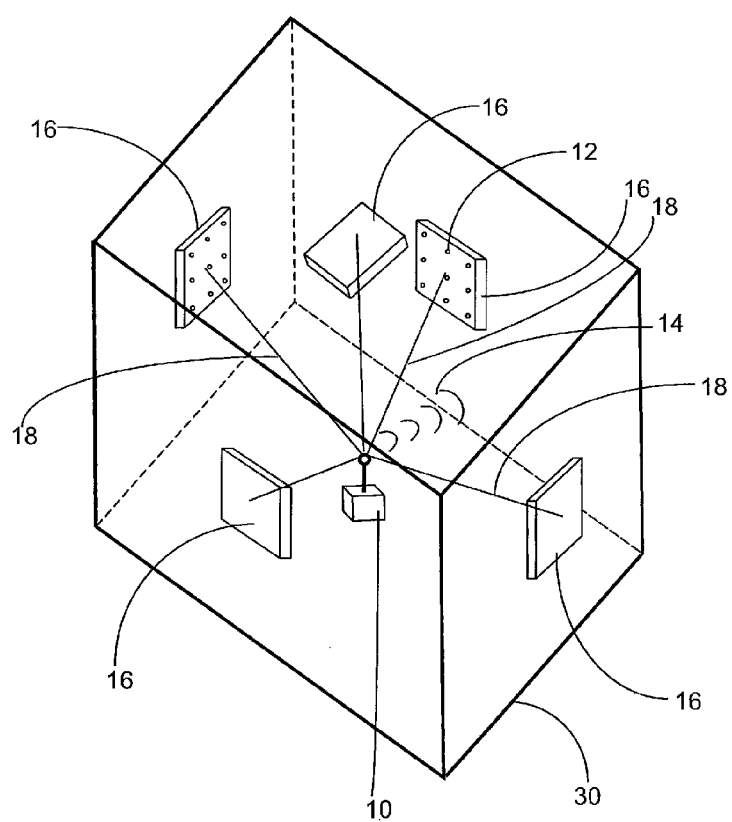
FIG. 3 is a schematic view of an exemplary transmitter in an operable configuration with a 3-dimensional lattice of receivers as a single array, or multiple arrays of said receivers situated around a room.

Another exemplary embodiment is shown in FIG. 3, with one or more receiver elements 12 or arrays 16 of signal receivers 12, affixed to a construct of multiple surfaces 30 (such as a 3-dimensional room) such that any number of signal transmitters 10 may be ranged if not obscured, for example by objects in the room between the signal receivers and the signal transmitters 10. The range processing may occur with a mathematical formula involving measured ranges 18, triangulation or trilateration algorithm, or the like.

Exemplary embodiments may operate in any wave medium where wave phenomena arise, such as IR near-far, visible, laser, ultra-violet, and high frequency radio waves, and combinations and various modulations thereof. Exemplary embodiments may also be applied to the acoustic medium and ultra-sonic waves. Further to this, the medium may operate to reflect the transmitted signal where the transmitter and receivers are operable from the same device or controlled by the same processing unit. An object that reflects the signal may need a suitable reflection medium (for example: such as reflecting metal surfaces or special IR reflecting tape) that allows for a calibratable or measureable range to be determined between the transmitter and receiver.

Referring to FIG. 1, short range precision ranging and positioning may be accomplished requiring a configuration as simple as a single transmitter 10 to a single or a plurality of individual signal receivers 12, in spaced relation and receiving the same transmitted signal 14. A single transmitter 10 may thus be operable to send a signal 14 including a series of primary bursts forming a train of pulses whose collective pulse profile and changes with increasing distance from the signal transmitter. Detecting and calibrating the changes in the collective pulse profile allows for range, distance and/or orientation to be correlated. In one example, the pulse profile is measured as a count of pulses in the signal and is converted to a value representative of a range 18, for example based on one or more calibration measurements. The 3-dimensional positioning calculation is hence based on a range 18 measurement from multiple signal receivers 12. This method of ranging and position measurement may occur accurately within a maximum range of 30 meters depending on the strength of transmitted signals and the sensitivity of the receiver. For electro-magnetic or acoustic mediums, methods according to exemplary embodiments herein are based on high frequency pulsing of these transmissions and using a receiver that is sensitive to and capable of digitally processing these pulsed signals. Estimates for the accuracy of ranging can be achieved for within 1 cm root-mean-square (RMS) error for 10 meter range, 1.0 mm RMS error for within 3 meters of range, and a range measurement resolution as low as 0.1 mm.

Figure 4:
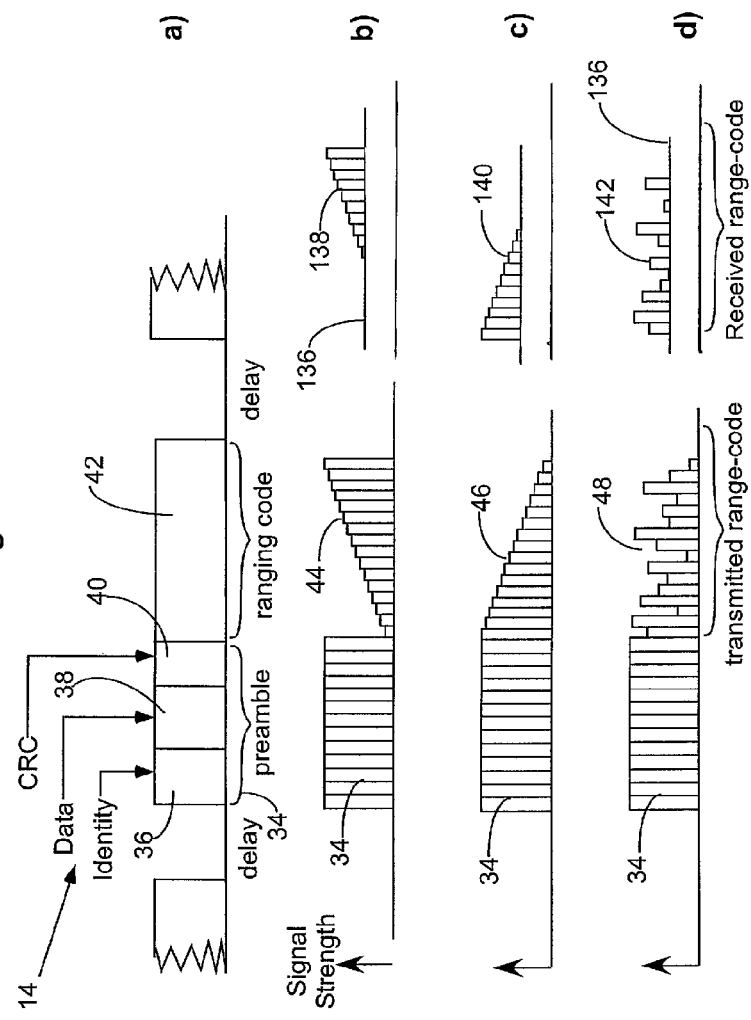
FIG. 4 is a schematic view of several exemplary plots of signals emitted by transmitters as defined herein.

Referring to FIG. 4, the signal 14 includes a digital preamble segment 34 allowing the receiver to identify the transmitter and to synchronize to a timing operation essential for ranging or pulse counting. The preamble segment 34 may, in this example, include all digital data fields, such as Device ID 36, operating data 38, encryption keys and a check-sum code, or generally a cyclic-redundancy code (CRC) 40, that is needed for the data communication between signal transmitter 10 and the signal receiver 12. The start of the data fields, for example, also allows the signal receiver 12 to begin synchronization and ranging.

The signal also includes a ranging segment 42 which provides ranging code that typically changes with increasing range 18 between the signal transmitter 10 and signal receiver 12, that is as the signal propagates toward the receiver in the carrier medium, such as atmospheric air. The ranging code is provided in the form of a series or train of pulses that vary in illumination strength along the series. The ranging segment may have various profile shapes including a series of ramped power levels incremented (as seen at 44 in plot b)) or decremented (as seen at 46 in plot c)) by the transmitter, as will be described. Another example may utilize pulses with randomly varying pulse strength (as seen at 48 in plot d)) In this case, the corresponding received ranging segments 138, 140 and 142 include the pulses above the predetermined threshold value 136, the count of which represents a direct measure of the illumination signal strength of the signal received, and hence the range. As will be described, the signal receiver 12 and those components, modules and functions associated therewith, are configured to receive the signal, identify the signal transmitter 10, and process the ranging segment 42 by counting the number of pulses present in the signal above a predetermined threshold value. The count then provides a representation of the distance, or range, between the signal transmitter 10 and the associated signal receiver 12, which may be applied to multiple signal transmitters 10 and receivers 12.

In one example, the positioning method makes use of a single transmitter pulsing at between 10 to 10,000 KHz. This range may vary for visible light or IR circuits using a transmitting diode and a receiving diode, but radio can vary significantly from 100 KHz upwards to 10 GHz. Each signal is thus transmitted in one or more primary bursts with a digitally coded sequence or a series of pulses at a rate of about 1 KHz to 500 KHz, with the burst rate being smaller than the pulse rate. Acoustic waves or pulses can vary from 10 Hz to 100 KHz for ultra-sonic ranges. Depending on the application, the duty cycle of the pulses inside the burst may be varied, allowing for the detector to operate more efficiently, although this should not adversely affect ranging or positioning accuracy thereof.

Figure 5:
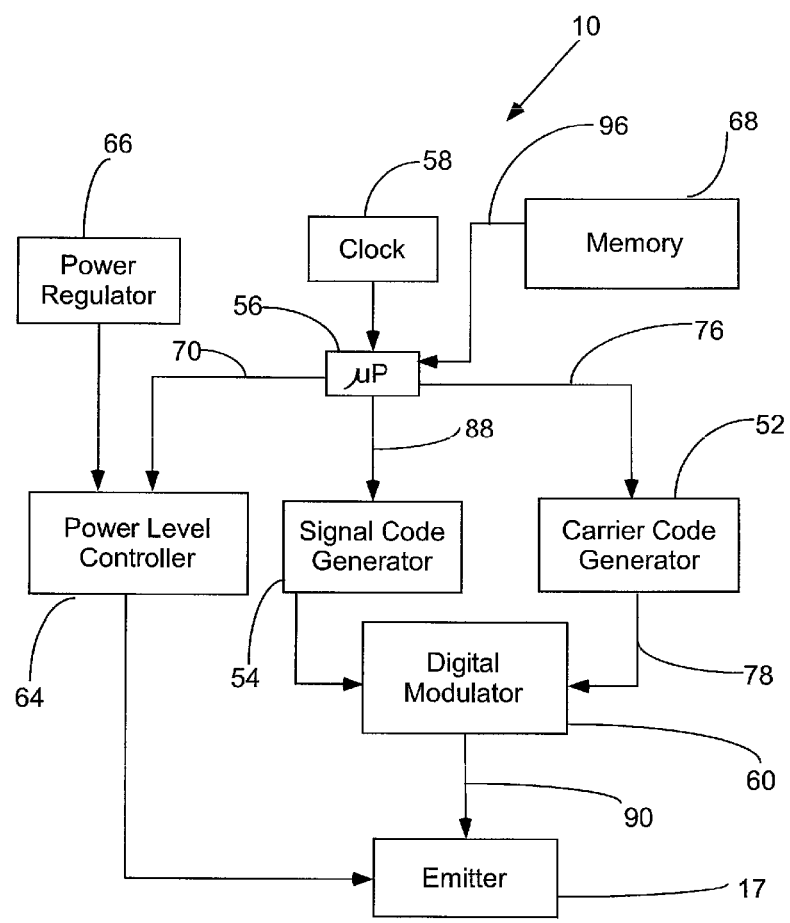
FIG. 5 is a schematic view of a portion of a transmitting device of FIG. 1.

In FIG. 5, each signal transmitter 10 includes a carrier code generator 52 and a signal code generator 54, in this case distinct processors under the control of a microprocessor 56 and synchronized by a common clock 58. Alternatively, the function of the carrier code generator 52 and the signal code generator 54 may be carried out in a common processor such as a general computer. Both the carrier code and signal code generators 52, 54 dispatch waveforms for the carrier and signal codes to a digital modular 60 which modulates the carrier and signal code waveforms to deliver a binary waveform to the emitter 17. A power level controller 64 receives ranging code details from the microprocessor 56 and regulated power from a power regulator 66 signal to adjust the power level of the output of the emitter 17 for signal transmission.

Figure 6:
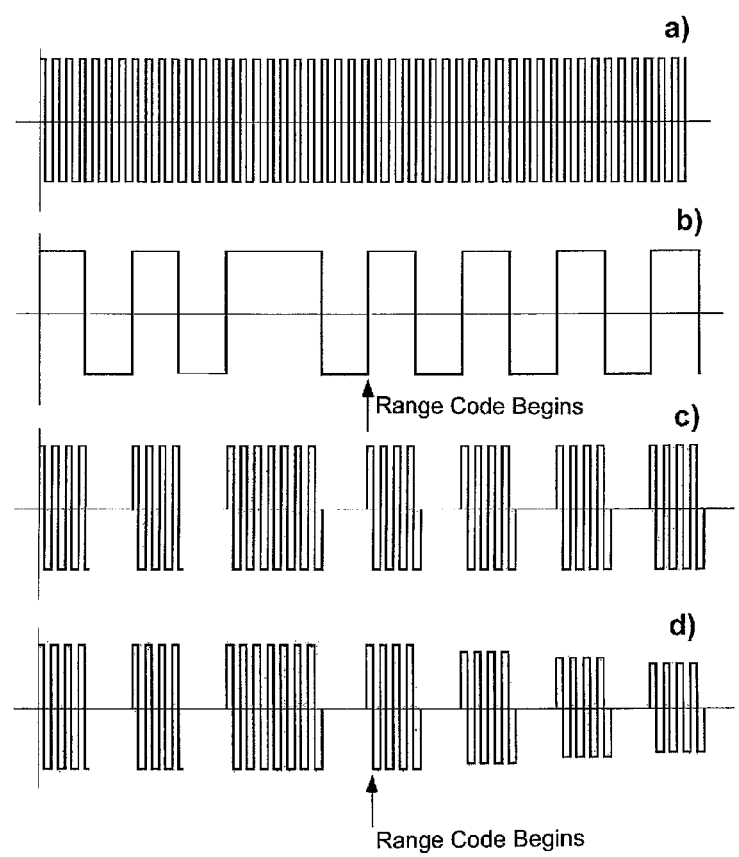
FIG. 6 is a schematic view of several additional exemplary plots of signals emitted by exemplary transmitters as defined herein.

Referring to FIGS. 5 and 6, the microprocessor 56 communicates with memory 68 for storage of transmitter identity and ranging code data. Alternatively, the ranging code data may be generated according to a ranging code algorithm in a corresponding processor. In this case, the carrier code includes instructions to the emitter 27, in the form of a digital waveform as shown in FIG. 6a), to be compiled by the digital modulator 60, to emit the carrier wave which will carry the signal. Similarly, the signal code includes instructions, in the form of preamble code, including code for the transmitter identity, the data field and the CRC field, as shown in FIG. 6b) to the digital modular, again to be compiled by the digital modular 60, to form a modulated digital output as shown in FIG. 6c) provided in the form of a waveform of binary ones and zeros each with a constant strength, peak or amplitude according to the operating power of the digital modulator 60.

Meanwhile, the microprocessor 56 dispatches instructions along path 70 to the power level controller 64 so that the power level controller 64 can set the power of each individual binary one in the waveform to form the amplitude of the emitter output as shown in FIG. 6d) as a series of pulses. The preamble segment 34 is shown with each of its pulses having a fixed maximum power, so that the entire preamble will be received by the receiver element above the predetermined threshold value. The ranging segment 42 is shown with the power level of each pulse being adjusted according to the ranging code.

Figure 7:
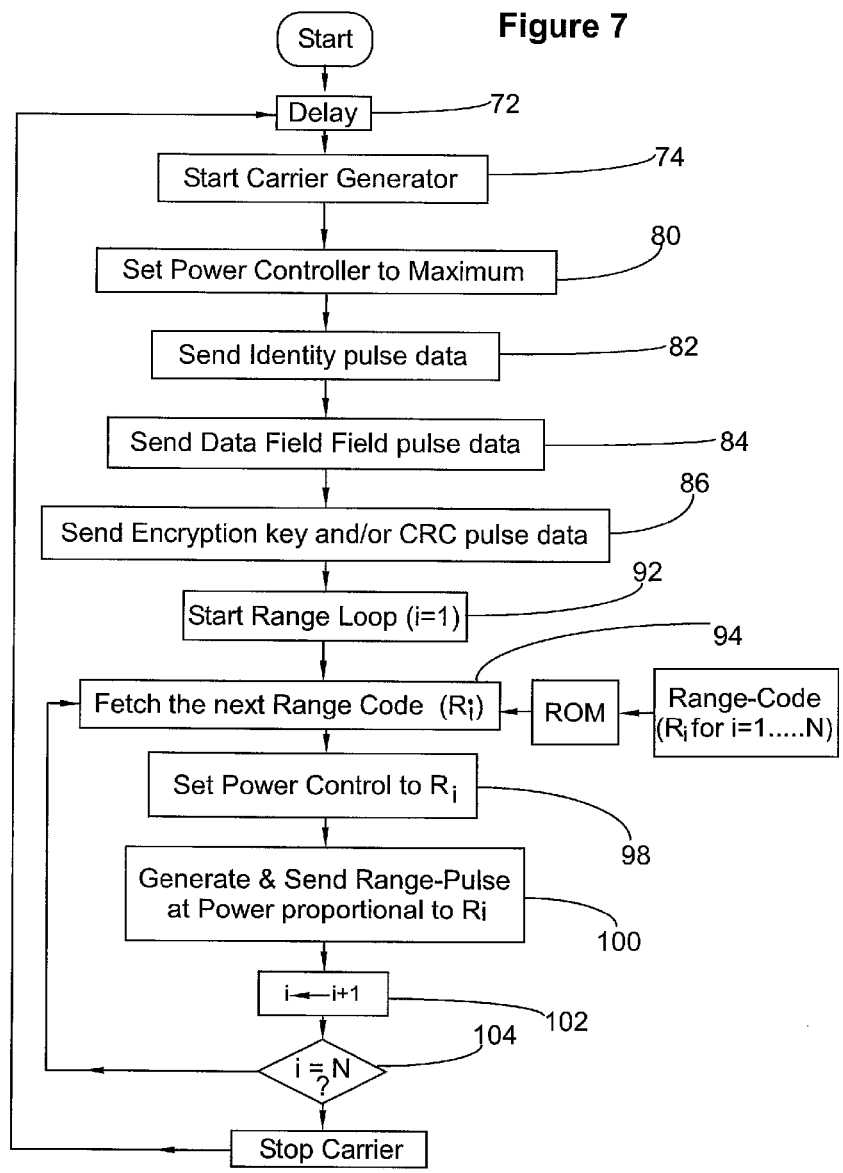
FIG. 7 is a flow chart of a process implementing the transmitter of FIG. 1.

Referring to FIG. 7 illustrates and exemplary process using an incremented ranging segment. The process of signal generation is started by the clock 58 executing a delay, at step 72, to denote the end of a previous signal. Next, at step 74, the microprocessor 56 instructs the carrier code generator 52, on data path 76, to initiate the carrier waveform on data path 78. The microprocessor 68, at step 80, instructs the power level controller 64, on data path 70, to set the power level to maximum. Next, at steps 82, 84 and 86, the microprocessor 56 instructs the signal code generator 54, on data path 88, to initiate the signal waveform by first dispatching the identity code waveform, then the data field code waveform, then the encryption and/or CRC pulse code waveform, which is then dispatched by the digital modulator 60 to the emitter 17 on data path 90. Next, at step 92, the microprocessor initiates a range loop and fetches, at step 94, the first range code stored in memory 68 via data path 96. With the first range code, the microprocessor 56 instructs the power level controller 64, at step 98, to set the first power level for the first pulse in the ranging segment, which in turn adjusts the power at the emitter output, at step 100, to form the first pulse in the train of the ranging segment. Next, at step 102, the microprocessor 56 advances the count and determines, at step 104, if the count equals N, the number of pulses in the range segment. If "no", then the microprocessor 56 repeats step 72 and fetches the range code for the next pulse in the ranging segment. Steps 94 to 104 are then repeated until the ranging segment has been fully formed on the emitter output, at which point, the emitter stops the waveform, at step 104, and terminates the signal, and the microprocessor repeats step 72 to implement the delay denoting the end of the signal.

The common clock 58 is not necessarily required but is strongly to ensure that, when the signal is received at the receiver array 16, there is no inconsistency between the bit-up times for the primary bursts, and hence the data carried in them. If the clocks for both the carrier code and signal code generators 52 and 54, respectively, are not synchronized, then an apparent jitter noise may appear in the timing of received primary bursts caused by the inconsistent count of received data. This may cause an increased "noise" in the ranging measurements causing reduced accuracy of ranging. Using a synchronizing clock 58 reduces, if not eliminates, this undesired source of ranging error.

Thus, the ranging code quantifies the power level of each individual pulse, according to a ranging algorithm. In one example, for incrementing the range-code the power function is $R(x)=x$, where $R(x)$ is a power level, and where x is the pulse number which increases from zero to N, and N is the maximum power level as well as the last pulse of the range-code. Similarly for a decrementing range-code the power function is $R(x)=N-x$. In another example, the nonlinear function of the range-code is the power function $R(x)=x^2/N$, as an increasing nonlinear range-code, and, $R(x)=N*(1-(x/N)^2)$ as a decreasing nonlinear range-code code. An example of an interleaved range-code is where the power function $R(x)=x$ (if x is an even number), $R(x)=N-x$ (if x is an odd number). This latter is an example of a range-code that will be calculated as an algorithm in a processor.

In this example, the ranging code is stored in memory 68 for each pulse. Electronic components are currently available that can be configured to set the power of a transmitting device digitally as a series of gated components inside a miniature integrated circuit substrate. Examples of such power controlling devices are digital resistors, gated field-effect transistors (FET's) with digitally controlled gain, digital-to-analog (DAC) devices, or the like. The power level controller 35, in this case, may use the ranging code and store it inside the power level controller's ROM for immediate setting of the power for the device. Hence, the power level controller 64 will set the power level of the signal emitter 17 during signal transmission, with each setting corresponding to an individual pulse. Typically the number of increments available for the power level settings is determined by the bit range of operation specified for the power level controller 64, and can be as low as 4-bits to as high as 10-bits long ranging from 16 settings to 1024 different power level control settings overall. Each power level controller setting translates into a transmitted signal strength setting for a single pulse, by precisely controlling the current or voltage flowing to the transmitter from a constant and controlled power regulator 106. It is desirable to maintain a consistent current flowing to the diode, so that the power regulator 106 be available to reduce the effects of battery drain that may otherwise change the precisely calibrated range settings of the transmitter 10 relative to the receivers 12.

Various methods of electronic circuitry are available that may be configured to serve as a power level controller in a transmitting device. Typically, the power level controller 64 adjusts the power level for each pulse within the ranging segment 42. Examples of devices using such methods of electronic circuitry include a Digital-to-Analog (DAC) chip and a digital resistor chip. Depending on the time required to adjust the strength of an individual pulse, a circuit must be able to process a digital instruction during the off-cycle of a pulse, allowing the digital power to be available during the next on-cycle for the next pulse. Such hardware devices for controlling signal strength depend on how the transmitting device best varies the signal strength, such as using voltage level, current level, or both, for example.

Figure 8:
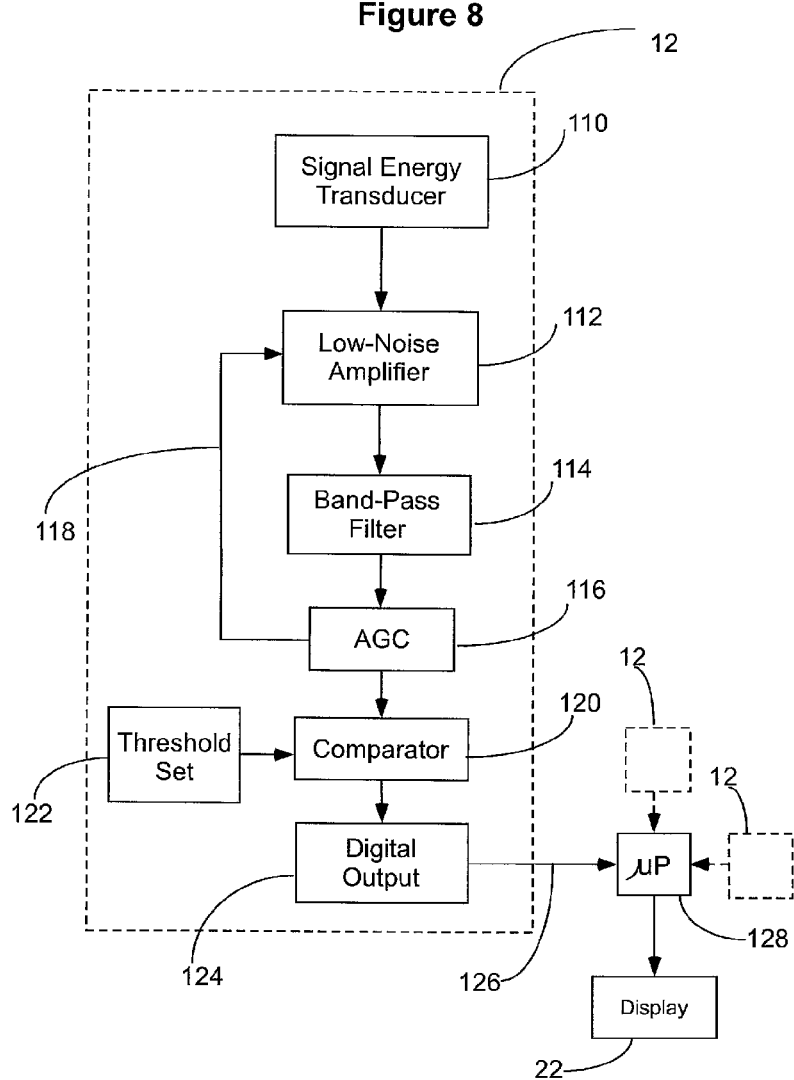
FIG. 8 is a schematic view of a portion of an exemplary receiver array of FIG. 1.

FIG. 8 illustrates more details of three receivers as examples of those in the array 16. Each signal receiver 12 includes a signal energy transducer 110 which receives the signal including the preamble and ranging segments and its carrier waveform and emits a corresponding series of secondary bursts digitally representing the signal These secondary bursts are, in turn, received by a low noise amplifier 112, in turn communicating with a band pass filter 114. The band pass filter 114 functions to isolate the value of each secondary burst from the carrier waveform. The band pass filter 114, in turn, communicates with an automatic gain controller (AGC) 116. The AGC 116 communicates along data path 118 to the amplifier 112 and the amplifier 112 with comparator 120. The comparator 120 receives a threshold setting value from a threshold set unit 122 and compares the messages from AGC 116 to establish the pulses in the range segment that are above the predetermined threshold and to dispatch corresponding instructions for each pulse above the predetermined threshold to the digital output unit 124 which in turn emits a digital output on path 126 to a microprocessor 128 for counting. The threshold set unit 122 may manually programmed or otherwise be calculated by way of another controller such as microprocessor 128 or a general purpose computer.

The microprocessor 128 is shown in more detail in FIG. 1 and includes a channel processor module 130, a range processor module 132 and an identity and position processor module 134. These modules, in this case, are subroutines operating within the microprocessor 128, or may alternatively be carried out by stand alone processors or in another computer system.

In this case, the channel processor 130 is configured to receive inputs on path 126 at frequencies of 10 to 10,000 KHz. In this case, the signal receiver 12 may require that the pulses in the range segment of the signal be sent at a "pulse rate" or frequency that allows the channel processor 130 to operate unimpeded without stray, interference, or ambient signals otherwise corrupting the received pulses.

The AGC 116 communicates on data path 118 to control the gain of the of the value being received by the comparator 120 and operate at a rate that is typically slower than the pulse rate, so as to not be altered by a lower frequency pulse rate. In effect, the role of the AGC 116 is to accommodate for the reduced strength of the range segment of the signal. The reduced strength simply means that the signal is losing its amplitude as the signal radiates from the signal transmitter 10 and through losses in the carrier medium, the farther the distance between the signal transmitter 10 and the signal receiver 12, the greater the gain provided by the AGC 116. The AGC 116 should change the gain relatively slowly in relation to the rate at which the pulses are received, so that the AGC 116 does not alter the ranging operation itself. If desired, the microprocessor 128 may be configured to control the gain provided by the AGC. The AGC 116 functions with the band-pass filter 114 which allows only secondary bursts to get through at the pulsed frequency, hence filtering out signal interference and ambient noise. The AGC 116 thus, in one operational phase, will only allow 1000 KHz pulses to pass through from the receiver's signal energy transducer 110. The AGC 116 may have other operational phases in which pulses of other frequencies may pass through, including those of a specified frequency or a specified range of frequencies. Generally speaking the secondary burst reception is digital and represented as burst codes that are received and processed with enough sensitivity that allow the receiver/transmitter combination to operate at long ranges in excess of 10 meters range, and with virtually no ambient IR interference. For example, a digital IR receiver diode, operating as the signal energy transducer 110, will operate to lock onto transmitted IR pulses to allow for the diode's AGC 116 to stay set inside the band-pass filter's cycle, allowing the digital pulse reception to not be interrupted or corrupted.

Equally important to the ranging segment transmitted from the signal transmitter 10, is that the signal receiver 12 allow for a programmable threshold of detection of individual pulses within the ranging segment. The receiver 12 is, in this example, in an OFF state when a pulse with a pulse strength below a threshold power level is received. The receiver 12 is configured to detect the transmitted pulse and transfer to an ON state, when the strength of the pulse exceeds the threshold power level. Ideally the variation of power level across the pulses in the train is configured to be proportional to the power loss due to increasing range between a transmitter and receiver. Otherwise, a power range should be selected that exceeds the power loss due to range changes. In this situation, only one calibration step may be required mathematically to select a suitable range given the available power levels and the programmed threshold.

Thus, in one exemplary embodiment, the ranging segment 42 provides a sequence of pulses, such as those shown at 44, 46 or 48. In the case of an incremental or ramp up sequence 44, at the beginning of each primary burst, the power level controller 64 is set initially to the minimum power setting. This causes the minimum amount of electrical power to flow through the signal transmitter 10, hence the transmitter 10 is transmitting energy at its minimum signal strength. At every off-cycle of the primary signal burst, the power level controller 64 is incremented a value which causes the transmitter power to gradually increase incrementally until it reaches the maximum power. At some time between the minimum and maximum signal strength or brightness of the transmitter, the receiver 12 switches on and begins receiving the primary pulses and converting them into a corresponding series of secondary bursts forming one or more digital messages. The microprocessor 128 then counts the digital messages in the ranging segment and this count is inversely proportional to range 18 between the transmitter 10 and receiver 12, that is, the smaller the counter, the greater distance travelled by the signal to the receiver 12.

In the case of multiple receivers 12 in the array 16, the AGC 116 for each receiver 12 may be controlled by a common control function. In this case, the individual AGC's 116 for each individual receiver 12 will not adjust independently of each of the others. This would mean that gain adjustment for signal loss is applied evenly across the receivers 12 to mitigate the possibility that some receivers 12 mistakenly identify a "gained" pulse signal to be above the predetermined threshold value, while another receiver, receiving the same pulse (but in this case not gained) consider the same pulse to be below the threshold, resulting in a different count and a different range that would otherwise not occur had the AGC's been adjusted consistently. Hence the error of range based location calculation may be significantly reduced, since the receivers, in this case, operate repeatably and consistently with each other. Such a multi-element AGC may thus allow the array to operate at long range and in the presence of external interference.

At the signal receiver 12, the varying strength of the pulses in the ranging segment 42 means that the signal receiver 12 may not activate until a threshold 136 is reached to receive pulses for counting. If the signal receiver (when switched-off) is in a consistent initial state (with a high AGC 116 setting for example) then there is a consistent threshold 136 that will trigger the receiver's ON state. This typically varies with the signal strength of the transmitter. However, the consistent state of the AGC 116 in the digital diode may in some cases require that a lower (or higher) pulse duty-cycle to keep it stable, or require a manual setting in the circuit to not vary with ambient light or other effects. In this case, the incremented, decremented and random pulse sequences are shown in a form as received by the receiver, at 138, 140, 142.

Receiver circuit components are currently available that may be configured for exemplary embodiments herein. For example the TSOP7000 from Vishay Electronics operates digitally for IR transmitted bursts at 455 KHz, and various radio devices such as a AD8302 Log-amp detector from Analog Devices will operate as a wideband radio receiver for radio bursts at any frequency within 1 KHz to 3 GHz. Standard IRDA modules have built-in AGC capabilities and allow for pulse transmitting and receiving at up to 4 MHz to allow for very fast and accurate ranging applications. These devices may be configured to receive a series or sequence of secondary burst signals to estimate the ranging in different media.

Figure 9:
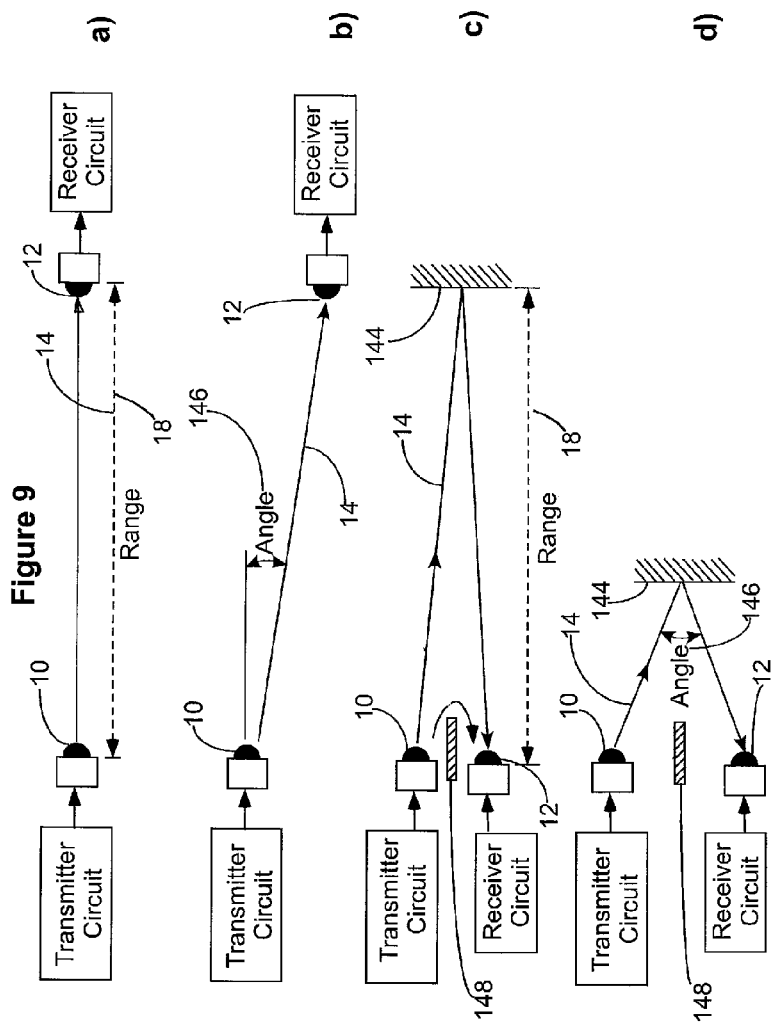
FIGS. 9A to 9D are schematic operational views of an exemplary transmitter and an exemplary receiver.

In an exemplary embodiment, as shown in FIG. 9A, the signal transmitter element 10 and signal receiver 12 are shown separated by the range 18. The signal receiver is configured to calculate the range 18 based on the signal 14 received from the signal transmitter circuit. This range is based on a constant and fixed angle between the signal transmitter and signal receiver. Similarly, in FIG. 9B, the signal receiver 10 is configured to calculate an angle 146 based on a signal 14 given that there is a fixed range. In FIG. 9C, the signal transmitter 10 is configured to send a signal 14 to reflect off a reflective barrier 144 and be received by the signal receiver 12, such that the range 18 may be calculated, assuming a constant and fixed angle 146 between the signal transmitter 10 and the signal receiver 12. In FIG. 9D, the signal 14 is reflected off barrier 144 and received by the signal receiver 12, such that the angle 146 may be calculated by the signal receiver 12, assuming a constant and fixed range between the signal transmitter and receiver. In both FIGS. 9C and 9D, an isolating barrier 148 is placed between the signal transmitter 10 and signal receiver 12 to reduce short-range cross-talk therebetween. Also, in FIGS. 9C and 9D, the signal transmitter and signal receiver may be operable in common circuitry providing the functions of both the transmitter and receiver.

In another exemplary embodiment, different types of sequences may be executed that the power level controller 64 may vary to create the required receiver count proportional to the range. Typically the ramped-up or ramped-down sequence is desirable depending on the behavior of the receiver's digital processing step. For a transmitter, the ramped-up power sequence 44 is better because the receiver circuit does not lag during the ramp-up cycle, nor does it alter the AGC 116 setting during a ramp-up. A ramp-down sequence 46 may typically alter the AGC 116 setting because the AGC 116 may attempt to hold lock if the received signal weakens causing inconsistent pulse counts in the microprocessor 128. If a decrement power control profile 46 is used instead, then a receiver 12 may receive digital pulses but turn-off as the power ramp weakens the signal (see FIG. 4). Typically the AGC 116 is set to fixed operation if a decremented power sequence 46 is used. Also, most digital devices suitable for the power level controller 64 may be better suited to increment or decrement because there is a shorter time to digitally switch gates for increment/decrement operations than having a whole new power setting written to its ROM. In other words, the ROM stores one power setting at a time for each pulse and is updated for each subsequent pulse.

As another exemplary embodiment, the power level or power control profile may use a sequence for the digital power that does not resemble a ramp 44, 46 that is neither increasing nor decreasing. This power control profile may, in this case, be patterned or random code 48 of power control such that all required values of digital power control are represented in the ranging segment 42 (see FIG. 6). Such a power code contains all the unique power control settings as found in a ramped code, for example, but ordered differently. The effect of this profile is that only a subset of all power settings are received by the receiver and hence the receiver pulse count is a subset of the pulses in the originating signal. The receiver's count is still proportional to the range 18 between the transmitter and receiver. A random or pseudo random code may be used. A code represented by a formula or an algorithm may also be used. This sequence of the power profile may be a random or patterned code for every ranging period 42, for each subsequent signal. It is possible that the code pattern 42 to 48 may be different for each successive ranging segment or period 42, assuming that the receiver properly decodes the patterned code into a count consistent with the range.

In an exemplary embodiment, a reason for using a random or patterned power control code 48 is to remove or average-out bias errors in the receiver unit. A receiver circuit may tend to "remember" the power profile of the previous cycle, that is the cycle that led to the immediately preceding pulse, as a biased AGC 116 setting or as a higher electrical capacitance in signal energy transducer or the light sensor circuit, for example. Also, when using light pulses, a signal energy transducer, in the form of a digital receiver diode has relatively fast switching speeds and may not require an AGC 116, in which case a sequence of random power settings 48 may be desirable for an emitter in the form of a transmitting diode, to offset any lingering electrical charge from the last pulse cycle. This will allow the power settings to not follow a known sequence that the receiving diode can adapt to easily. In this configuration, the received pulses in the burst are still counted as digital output pulses and the sum is proportional to the signal strength and hence the range. The disadvantage is that a power control device cannot write digital control values to the ROM as fast as they can be either incremented or decremented.

There are various types of device configurations possible using the above mentioned single transmitter and receiver(s) combination, including:

1) a single transmitter 10 sending signals 14 to a single signal receiver 12 measuring the signal strength and range.
2) a single transmitter 10 sending signals 14 to an array 16 of two signal receivers 12 to determine spaced relation between the two signal receivers 12. This is a 2-dimensional positioning method.
3) a single transmitter 10 sending signals 14 to an array 16 of three or more signal receivers 12, such as a symmetrical array configuration of signal receivers 12. This may be a 2- or 3-dimensional positioning method, depending on the orientation of the signal receivers 12.
4) a single transmitter 10 sending signals 14 to an array 16 of many signal receivers 12 to allow a least-squares fit of the transmitter ranges and arranged as a profile 60 (FIG. 10) to deduce the angular of curvature of the transmit profile 60, hence deducing angle of arrival and position.
5) a single transmitter 10 sending signals 14 to at least two arrays 4 of signal receivers 12 that allows for a least-squares solution fitting the spatial power profile of the transmitting device 10 to determine the angular orientation of the transmitting device in 3-dimensions, and hence allowing to use a curvature profile 150 (FIG. 10) to deduce the position of the transmitter 10 in addition to the ranging measurements 18 at each said signal receiver 12.

In exemplary embodiments, angular orientation may be expressed as the elevation and heading angles to be determined for a transmitter 10, by determining multiple ranges from a single transmitter 10 to multiple signal receivers 12, and hence fitting a surface of these ranges and using a curvature profile 150 to determine the device position.

In an exemplary embodiment, an orientation angle estimation method may be implemented, based on the use of a multi-receiver array processing of range results with multiple channels. For instance, outputs of range 18 from multiple channels, where each channel receives the output from one of a number of receivers (such as in a 3×3 (9 sensor) array or a 4×4 (16 sensor) array) The output result may be used to present will be a 3×3 array image or a 4×4 array image representing the estimated range between the transmitter 10 and the array 16, in this case providing a planar array. By fitting a surface curvature profile 150 through the range data points with coordinates of the actual positions of the sensors on the array, an estimate for an illumination lobe profile, as shown in FIG. 10, of the transmitter may be calculated. Depending on the size of the sensor array, greater accuracy can be obtained for the angle estimate including more precision calculation of the XYZ coordinates of the transmitter. An example of the angle orientation estimation method and apparatus is depicted in FIG. 10.

In an exemplary embodiment, a single transmitter 10 may be used with multiple emitters 17 to determine the orientation of a device in 3-dimensions, as shown in FIG. 11. Using three distinct emitters 17 multiplexed, by way of multiplexer 160, from one transmitter 10 and each identifiable by a code 36 in the transmitted preamble 34 and data field 38 of the transmission, multiple emitters 17 may be multiplexed with a round-robin algorithm built into the transmitting device's processor 56, or activated using a wireless controller 162 instructing the transmitter 10 to independently transmit to one of three separate emitters 17. At the receiver array 16 each independent transmitter 10 is positioned and tracked in 3-dimensional space. If three distinct transmitter element 17 coordinates are available then the transmitter 10 can be positioned accurately in 3-dimensional space, as well the orientation angles (roll, pitch, and yaw) can be determined. However, if a single transmitter element 17 is not present then the processing computer may employ an algorithm to estimate the said transmitter element's position based on past or proximity data. A computer algorithm may "correct" for anomalies in the calculation by estimating the position of the unknown transmitter element, knowing that it is within proximity to the other two transmitter elements 17. An example of this method of device positioning is depicted in FIG. 11 for a single transmitter 10 with three signal emitters 17 also showing a 3-dimensional rendering of a multi-point image or icon 24 on the display unit 22.

In an exemplary embodiment, a single transmitter 10 may be used to calculate the range to multiple arrays 16 situated on the walls around a room, as shown in FIG. 3, for example. These ranges may be used to form a triangulation or trilaterated solution using a minimum of three ranges representing the intersection of three circular surfaces. If more ranges are available then a least-squares solution may be used to determine the XYZ coordinates of the transmitter 10. This approach is similar to the Global Positioning System (GPS) method but instead pseudo-ranges are determined in a short-range signal environment. If the range measurements are biased because of the choice of the power control method and code, then a pseudo-range and bias estimation algorithm may be used to improve positioning accuracy.

In an exemplary embodiment, a method may be employed for determining the dilution of precision, a principle used in GPS calculations. This is based on multiple sensor processing channels allowing the solution of the transmitter to be over-determined. For example, if a 2×2 array is used then there are four equations to determine a unique XYZ coordinate calculation where only three unknown values are available. Thus, using an extra equation allows a measure of solution dilution to be calculated related to the uncertainty or over-determined nature of the solution available. Thus, for example, if one sensor was partially obscured or occluded then the result will cause an inaccurate least-squares solution to be calculated. This solution result will be measured as a solution with diluted precision, and the uncertainty will be measured beyond an acceptability threshold and thus allowing the solution to be ignored. Dilution of precision is common in GPS position measurement and is usually the result of poor calculation based on high multi-path fading or loss of satellite signals in urban canyons, for example.

While only specific combinations of the various features and components of exemplary embodiments have been discussed herein, it will be apparent to those of skill in the art that desired subsets of the disclosed features and components and/or alternative combinations of these features and components can be utilized, as desired. For example, it is to be stressed that the configurations and quantities of transmitter devices 10 and signal receivers 12 is not particularly limited, and can be chosen and structured for any given application in any desired manner. Thus, where it is only desired to determine a location of a single object in a single plane, the array can be limited to two receiver units 12 (connected to two single channel processors via a wired interface) that interact with (or receive signals from) one transmitter device 10 that is affixed to that single object. In contrast, where it is desired to track the location and/or movement of a plurality of objects in a three dimensional space, then the array can consist of a plurality of signal receivers 12 (each being coupled to a respective channel processor) that are configured to interact with a plurality of transmitter devices 10, each affixed to its own object. Using suitable programming logic in the processor, a direction can be calculated based on a different range to each receiver. For example, in a configuration with one transmitter 17 and two signal receivers 12, and denoting R1 and R2 as the reflected ranges to each respective receiver from the one transmitter, the processor can switch to an "ON" state if R1 is greater than R2, otherwise "OFF" if R2 is greater than R1. For example, proximity light switch, or a directional light switch, or any other two state switch apparatus may employ this configuration.

It should now be apparent to those of skill in the art that teachings herein can be used in a wide variety of real-world applications. FIGS. 12A and 12B illustrate exemplary embodiments in the form of a mouse 172 and a pointing device 174. In another exemplary embodiment, FIG. 13 illustrates a gesture interface 170 that may be utilized as a human interface device for computer applications, as an alternative to the mouse and pointing devices of FIGS. 12A and 12B, and potentially the need even for a computer keyboard, as software used on a computer system connected to gesture interface 170 may be programmed to respond to a sophisticated range of hand gestures that could represent the keys on a computer keyboard. In this manner, gesture interface 170 can mimic an actual computer keyboard. A IR-based hand gesture recognition device would typically involve a receiver array with an IR emitter in the middle allowing gestures to be determined by a combination of IR reflections as unique range-based spatial or temporal patterns recorded by the receiver array. Examples of gestures intuitively recognized from a human hand are "push", "grab", "expand", and "swipe" (any direction). A microprocessor can recognize the unique patterns and display them on a computer screen, or perform a representative action.

It is also contemplated that transmitting devices, such as transmitting device 10 and emitter 17, may be fixed while an array of receivers 12 may be mobile and/or worn or carried by a user. Such a configuration may be used to allow a user to obtain precise positioning information for a mobile display allowing interactive input to a gaming device, for example, and vice versa. As another example, an array of receivers 12 could be mounted on a personal digital assistant (or other portable computing device) that is carried by an individual. At the same time, a plurality of transmitting devices 10 can be mounted throughout a shopping mall. As the user walks through the shopping mall, the personal digital assistant can provide precise mapping information to the user, indicating to the user exactly where the user is located within the shopping mall. Other applications of having mobile receivers 12 will now occur to those of skill in the art. It should now also be apparent that applications can exist where both transmitting devices 10 and an array of receivers 12 are both mobile.

In another exemplary embodiment, an array of transmitting devices 10 and an array 16 of receivers 12 may be configured so that, in at least one mode of operation, each are intended to be fixed in relation to the other, with a computing device associated with the system being configured to detect whether any movement in the fixed relation occurs. For example, such a system can be used in a burglar alarm system, where transmitting devices 10 are affixed to doors and windows, and the array 16 of receivers 12 are affixed to a wall 30 or other stationary fixture proximal to the transmitting devices. When the burglar alarm system is "armed", the movement of a door or window can be detected and provided as a signal to activate the alarm.

The configuration of receivers 12 in FIG. 3 depicts a three-dimensional cube of receivers 12. Such a configuration of receivers 12 may be used in a room, or multiple rooms of a building. Transmitters 10 that are active within the room can then be affixed to objects (or persons), to track their location within the room (or the entire building if the building is so equipped). In this example, a display unit may be replaced with computer tracking software that keeps track of where those objects are located in that room. This particular system can be duplicated in each room of the building, and wherein each array 16 of receivers 12 in the building is linked together wired or wirelessly, thereby providing a means for tracking the location of objects (or persons) as they move throughout the entire room or building. For example, an entire shopping mall could be outfitted with a plurality of arrays 16 of receivers 12, and individual customers provided with transmitting devices 10, thereby providing a means to track the movement, and thereby the shopping patterns, of particular individuals.

In an exemplary embodiment, it is also contemplated that every transmitting device 10 that is operable with multiple different arrays of receiver units 12 may be uniquely coded, in the preamble segment 34, thereby providing a means to track every individual transmitting device 10 in a centralized or master database. Such unique coding can include encryption or other security measures to allow them to be properly authenticated to operate with corresponding receiver units 12.

It is also contemplated, for exemplary embodiments, that the teachings herein can be applied to surgical procedures. For example, transmitting devices 10 can be affixed to a surgical instrument or implantable medical device and to various biological landmarks inside the patient. An array of receivers 12 proximal to the operating arena can then be connected to a computing device to give data as to where the surgical instrument or medical device is located in relation to the biological landmark. For example, a small radio transmitter device 10 (or a plurality thereof) can be affixed at a blockage point in an artery. A second transmitter device 10 (or a plurality thereof) can be affixed to a stent to be implanted at the blockage point. During insertion of the, stent, the array of receiver units 12 can communicate with the stent and the blockage point to ensure proper locating of the stent.

Another exemplary embodiment includes a directional light-switch and dimmer apparatus. Using a transmitting device 10 affixed between two signal receivers 12 such that the emitted signal reflects off from a moving object in such a manner that one signal receiver receives a low-range reflection before another, allows for a directional object motion to be determined. A microprocessor may employ suitable detection logic to determine a switch ON state based on one directional movement, and a switch OFF state as the opposite directional movement. Dimming of a light intensity, for example, may be based on the range measurement using both receivers simultaneously when the switch is in the ON state.

Another example of applicability of various exemplary embodiments herein is the field of industrial robotics. An individual robot on an assembly line can be outfitted with a plurality of transmitting devices 10, typically located at points on the robot that can move. The array of receiver units 12 and associated processing electronics that are proximal to the robot can then determine, with great precision, where the robot is located in an absolute terms. This location data can then be fed back to ensure precise locating of the robot is effected in the software and machinery used to move the robot, and thereby obviate the limitations of relying on relative positioning determinations that are effected by measuring the number of turns of a servo motor controlling the robot.

Another example of applicability of various exemplary embodiments herein is the field of golf swing analysis. A golf "mat", shown at 176 in FIG. 14, may be outfitted with transmitting devices 10 to emit a signal that reflects off from the golf club foot, such that the reflected signals are received by suitable array of receiver units 12. The reflected path is measured and used to determine the position of the club foot, hence the club foot path can be calculated, yielding useful information to the golfer for swing practice purposes. Useful information to be discerned are the club swing speed (typically up to 100 MPH), alignment relative to a centerline, and the height of the swing arc relative to a golf ball positioned in the mat area. The range capture speed must be up to 10,000 samples per second to accurately capture a fast golf swing for analysis purposes.

Another example of applicability of various exemplary various embodiments herein is the emerging field of immersive reality, wherein a user is equipped with a virtual reality display helmet and then equipped with one or more gesture interfaces 170, and as such may use a 6DOF controller 180 as shown in FIG. 14. Where the user has a transmitting device 10 affixed to all limbs and fingers, a computing device that interconnects the array of receiver units 12 and the virtual reality display helmet can present an immersive reality experience to the user.

FIG. 16 shows a general computer system 190 on which exemplary embodiments may be practiced. The general computer system comprises information relay module 192. In some embodiments, the information relay module 192 comprises a module for providing audible cues, such as speakers via sound card 218. In some embodiments, the information relay module includes a display device or module 194 with a display screen 196. Examples of display device are Cathode Ray Tube (CRT) devices, Liquid Crystal Display (LCD) Devices etc. The general computer system can also have other additional output devices like a printer. The cabinet 198 houses the additional basic components of the general computer system such as the microprocessor, memory and disk drives. In a general computer system the microprocessor is any commercially available processor of which x86 processors from Intel and 680X( ) series from Motorola are examples. Many other microprocessors are available. The general computer system could be a single processor system or may use two or more processors on a single system or over a network. The microprocessor for its functioning uses a volatile memory that is a random access memory such as dynamic random access memory (DRAM) or static memory (SRAM). The disk drives are the permanent storage medium used by the general computer system. This permanent storage may be a magnetic disk, a flash memory and a tape. This storage may be removable like a floppy disk or permanent such as a hard disk. Besides this the cabinet 198 may also house other additional components like a compact disc read only memory (CD-ROM) drive, sound card, video card etc. The general computer system may also include various input devices such as, for example, a keyboard 200 and a mouse 202. The keyboard and the mouse may be connected to the general computer system through wired or wireless links. The mouse 202 may be a two-button mouse, three-button mouse or a scroll mouse. Besides the said input devices there may be other input devices like a light pen, a track ball, etc. The microprocessor is configured to execute a program called the operating system for the basic functioning of the general computer system. The examples of operating systems are UNIX™, WINDOWS™ and OS X™. These operating systems allocate the computer system resources to various programs and help the users to interact with the system. It should be understood that the disclosure is not limited to any particular hardware comprising the computer system or the software running on it.

FIG. 17 shows the internal structure of the general computer system of FIG. 15. The general computer system 190 includes various subsystems interconnected with the help of a system bus 204. The microprocessor 206 communicates and controls the functioning of other subsystems. Memory 208 helps the microprocessor in its functioning by storing instructions and data during its execution. Fixed drive 210 is used to hold the data and instructions permanent in nature like the operating system and other programs. Display adapter 212 is used as an interface between the system bus and the display device 194, which is generally a monitor. A network interface 214 is used to connect the computer with other computers on a network through wired or wireless means. The system is connected to various input devices like keyboard 200 and mouse 202 and output devices like a printer 216 or speakers. Various configurations of these subsystems are possible. It should also be noted that a system implementing exemplary embodiments may use less or more number of the subsystems than described above. The computer screen which displays the results can also be a separate computer system than that which contains components such as a database and the other modules described above.

Other exemplary embodiments are also provided as described below:

In an exemplary embodiment, there is provided a signal transmitting device for conveying a signal for use in determining a distance between the signaling device and a remote location, comprising a source transmitter operable to transmit a train of pulses forming a data stream representing a message including a series of preamble pulses having a common carrier frequency and a relatively constant pulse strength, the series of preamble pulses having a pattern corresponding to a predetermined preamble segment of the message, the data stream including a series of body pulses representative of a body segment of the message, the body pulses including a common carrier frequency with the header pulses, each of the body pulses having a pulse strength, the pulse strength varying across the series of body pulses in a predetermined pulse strength pattern.

In an exemplary embodiment, there is provided a device as defined, the source transmitter being operable for generating a series of body pulses with a progressively increasing pulse strength.

In an exemplary embodiment, there is provided a device as defined, the source transmitter being operable for generating a series of body pulses with a progressively decreasing pulse strength.

In an exemplary embodiment, there is provided a device as defined 1, the source transmitter being operable for generating a series of body pulses with a varying pulse strength from one pulse to another in the series.

In an exemplary embodiment, there is provided a device as defined, the source transmitter being operable for generating a series of body pulses with a varying pulse strength from one pulse to another in the series, according to a fixed or varying pattern In an exemplary embodiment, there is provided a device as defined, the source transmitter being operable for generating a series of body pulses with a varying pulse strength from one pulse to another in the series according to a predetermined algorithm.

In an exemplary embodiment, there is provided a device as defined, the source transmitter being operable with carrier frequencies including near infrared, far infrared, visible, laser, ultra-violet, high frequency radio, ultrasonic, and combinations and modulations thereof.

In an exemplary embodiment, there is provided a device as defined, the source transmitter being operable to deliver the series of header and body pulses at pulsing speeds ranging from 10 to 10,000 KHz for pulses transmitted at visible light or infrared carrier frequencies, from 100 KHz to 10 GHz for pulses transmitted at radio carrier frequencies, and from 10 Hz to 100 KHz for pulses transmitted at ultra-sonic carrier frequencies.

In an exemplary embodiment, there is provided a device as, the preamble segment including unique identity including one or more unique data field code-words assigned to the source transmitter.

In an exemplary embodiment, there is provided a device as defined, wherein the signals are identifiable by at least one preamble or data field identity code, operational data field, time-synchronizing data code, and/or ranging code.

In an exemplary embodiment, there is provided a device as defined, the signal including a signal ranging code, wherein the different versions of the pulse pattern are identifiable using variable radiated signal strength that is varied in a sequence which includes the actual data code.

In an exemplary embodiment, there is provided a device as defined, wherein the transmitter is affixed to a pointing device and the electronic circuit is coupled with an input device operatively associated with a personal computer having a display device and such that the pointing device is operable to move a cursor on the display device.

In an exemplary embodiment, there is provided a device as defined, the source transmitter including a carrier code generator to generate a carrier waveform, a signal code generator to generate a signal waveform.

In an exemplary embodiment, there is provided a device as defined, the signal code generator configured to generate a signal waveform, including an identity code waveform and a data field code waveform together or in succession.

In an exemplary embodiment, there is provided a device as defined, the signal code generator configured to generate an encryption waveform.

In an exemplary embodiment, there is provided a device as defined, the signal code generator configured to generate a signal waveform, including a identity code waveform, a data field code waveform and/or an encryption waveform together or in succession.

In an exemplary embodiment, there is provided a device as defined, the signal code generator configured to generate a ranging segment waveform.

In an exemplary embodiment, there is provided a device as defined, the signal code generator configured to generate a signal waveform, including a identity code waveform, a data field code waveform an encryption waveform, and/or a ranging segment waveform, together or in succession.

In an exemplary embodiment, there is provided a device as defined, the signal code generator configured to generate a signal waveform.

In an exemplary embodiment, there is provided a device as defined, further comprising a processor, the processor configured to control the generation of a signal waveform including a ranging segment waveform, according to a power function, $R(x)=x$, where $R(x)$ is a power level, and where x is a pulse number which increases from zero to N, and N is a maximum power level.

In an exemplary embodiment, there is provided a device as defined, further comprising a processor, the processor configured to control the generation of a signal waveform including a ranging segment waveform, according to a power function, $R(x)=N-x$, where $R(x)$ is a power level, and where x is a pulse number which increases from zero to N, and N is a maximum power level.

In an exemplary embodiment, there is provided a device as defined, further comprising a processor, the processor configured to control the generation of a signal waveform including a ranging segment waveform, according to a power function, $R(x)$ as an increasing and/or decreasing, nonlinear and/or linear range-code, or an algorithm carrying out one or more subroutines to select or identify elements of the ranging segment waveform.

In an exemplary embodiment, there is provided a device as defined, the processor communicating with a power level controller, the carrier code generator, the signal code generator and the power level controller communicating with an emitter for emitting the signal.

In an exemplary embodiment, there is provided a device as defined, the power level controller configured to set a corresponding power level for each pulse in the ranging segment being according to instructions received from the processor.

In an exemplary embodiment, there is provided a device as defined, further comprising a memory for storing values of R(x), the values accessible to the processor and/or the power level controller.

In an exemplary embodiment, there is provided a device as defined, the signal including a signal strength code for receiving the amplitude information, a transmitter detector code for determining an identity of the transmitting device, a data signal extractor code for determining any specific data embedded in the radio signal respective to the transmitting device.

In an exemplary embodiment, there is provided a device as defined, the source transmitter including a power supply, a signal strength code generator, a carrier code generator interconnected by a signal modulator; the transmitter device further comprising a pulse shaping module for shaping a waveform output from the signal modulator; the transmitter device further comprising a wave emitter connected to an output of the pulse shaping modulator for outputting the signal.

In an exemplary embodiment, there is provided a device as defined, the wave emitter including an infra-red or light emitting diode, a laser emitter, a radio antenna and/or a piezocoupler.

In an exemplary embodiment, there is provided a device as defined, the signal code generator being coupled to a microprocessor.

In an exemplary embodiment, there is provided a device as defined, the signal code generator further comprising a switch for selectively changing the signal strength code to another code when the switch is activated.

In an exemplary embodiment, there is provided a device as defined, wherein the transmitter device is incorporated into a light switch, a computer interface including a mouse, a tilt-joystick, a pointer controller, a six-degree-of-freedom interface, or a gesture interface.

In an exemplary embodiment, there is provided a device as defined, wherein the transmitter is incorporated into a surgical instrument.

In an exemplary embodiment, there is provided a device as defined, wherein the transmitter is incorporated into an industrial robot, a golf mat, or speed measurement device.

In an exemplary embodiment, there is provided a signal receiving device for receiving a signal from a signal transmitting device for determining a position and/or range of a remote location relative to a source location, comprising a receiver to be located at the remote location, the receiver operable to receive the signal, the signal including a train of pulses forming a data stream representative of a message, the train of pulses including a series of preamble pulses having a common carrier frequency and a relatively constant pulse strength, the series of preamble pulses having a pattern corresponding to a predetermined preamble segment of the message and a series of body pulses, the body pulses having a common carrier frequency with the header pulses and representative of a body segment of the message, each of the body pulses having a pulse strength, the pulse strength varying across the series of body pulses in a predetermined pulse strength pattern, the receiver being operable to identify the body pulses received in the train of pulses above a predetermined body pulse strength threshold value.

In an exemplary embodiment, there is provided a device as defined, the receiver being operable to count body pulses received in the train of pulses above the predetermined body pulse strength threshold value, the count indicative of the position and/or range.

In an exemplary embodiment, there is provided a device as defined, the preamble segment including unique identity including one or more unique data field code-words assigned to the source transmitter.

In an exemplary embodiment, there is provided a device as defined, wherein the signals are identifiable by at least one preamble or data field identity code, operational data field, time-synchronizing data code, and/or ranging code.

In an exemplary embodiment, there is provided a device as defined, the signal including a signal ranging code, wherein the different versions of the pulse pattern are identifiable using variable radiated signal strength that is varied in a sequence which includes the actual data code.

In an exemplary embodiment, there is provided a device as defined, wherein the transmitter is affixed to a pointing device and the electronic circuit is coupled with an input device operatively associated with a personal computer having a display device and such that the pointing device is operable to move a cursor on the display device.

In an exemplary embodiment, there is provided a device as defined, the source transmitter including a carrier code generator to generate a carrier waveform, a signal code generator to generate a signal waveform.

In an exemplary embodiment, there is provided a device as defined, the signal code generator configured to generate a signal waveform, including an identity code waveform and a data field code waveform together or in succession.

In an exemplary embodiment, there is provided a device as defined, the signal code generator configured to generate an encryption waveform.

In an exemplary embodiment, there is provided a device as defined, the signal code generator configured to generate a signal waveform, including a identity code waveform, a data field code waveform and/or an encryption waveform together or in succession.

In an exemplary embodiment, there is provided a device as defined, the signal code generator configured to generate a ranging segment waveform.

In an exemplary embodiment, there is provided a device as defined, the signal code generator configured to generate a signal waveform, including a identity code waveform, a data field code waveform an encryption waveform, and/or a ranging segment waveform, together or in succession.

In an exemplary embodiment, there is provided a device as defined, the signal code generator configured to generate a signal waveform.

In an exemplary embodiment, there is provided a device as defined, further comprising a processor, the processor configured to control the generation of a signal waveform including a ranging segment waveform, according to a power function, $R(x)=x$, where $R(x)$ is a power level, and where x is a pulse number which increases from zero to N, and N is a maximum power level.

In an exemplary embodiment, there is provided a device as defined, further comprising a processor, the processor configured to control the generation of a signal waveform including a ranging segment waveform, according to a power function, $R(x)=N-x$, where $R(x)$ is a power level, and where x is a pulse number which increases from zero to N, and N is a maximum power level.

In an exemplary embodiment, there is provided a device as defined, further comprising a processor, the processor configured to control the generation of a signal waveform including a ranging segment waveform, according to a power function, $R(x)$ as an increasing and/or decreasing, nonlinear and/ or linear range-code, or an algorithm carrying out one or more subroutines to select or identify elements of the ranging segment waveform.

In an exemplary embodiment, there is provided a device as defined, the processor communicating with a power level controller, the carrier code generator, the signal code generator and the power level controller communicating with an emitter for emitting the signal.

In an exemplary embodiment, there is provided a device as defined, the power level controller configured to set a corresponding power level for each pulse in the ranging segment being according to instructions received from the processor.

In an exemplary embodiment, there is provided a device as defined, further comprising a memory for storing values of R(x), the values accessible to the processor and/or the power level controller.

In an exemplary embodiment, there is provided a device as defined, the signal including a signal strength code for receiving the amplitude information, a transmitter detector code for determining an identity of the transmitting device, a data signal extractor code for determining any specific data embedded in the radio signal respective to the transmitting device.

In an exemplary embodiment, there is provided a device as defined, the source transmitter including a power supply, a signal strength code generator, a carrier code generator interconnected by a signal modulator; the transmitter device further comprising a pulse shaping module for shaping a waveform output from the signal modulator; the transmitter device further comprising a wave emitter connected to an output of the pulse shaping modulator for outputting the signal.

In an exemplary embodiment, there is provided a device as defined, the wave emitter including an infra-red or light emitting diode, a laser emitter, a radio antenna and/or a piezo-coupler.

In an exemplary embodiment, there is provided a device as defined, the signal code generator being coupled to a microprocessor.

In an exemplary embodiment, there is provided a device as defined, the signal code generator further comprising a switch for selectively changing the signal strength code to another code when the switch is activated.

In an exemplary embodiment, there is provided a device as defined, wherein the transmitter device is incorporated into a light switch, a computer interface including a mouse, a tilt-joystick, a pointer controller, a six-degree-of-freedom interface, or a gesture interface.

In an exemplary embodiment, there is provided a device as defined, wherein the transmitter is incorporated into a surgical instrument.

In an exemplary embodiment, there is provided a device as defined, wherein the transmitter is incorporated into an industrial robot, a golf mat, or speed measurement device.

In an exemplary embodiment, there is provided a system for range finding between a signal transmitter and a signal receiver comprising:

a signal transmitter operable to transmit a ranging signal having train of pulses forming a data stream representing a ranging message including a series of preamble pulses having a common carrier frequency and a relatively constant pulse strength, the series of preamble pulses having a pattern corresponding to a predetermined preamble segment of the message, the data stream including a series of body pulses representative of a body segment of the message, the body pulses having a common carrier frequency with the header pulses, each of the body pulses having a pulse strength, the pulse strength varying across the series body pulses in a predetermined pulse strength pattern, one or more signal receivers to be located at the remote location, the receiver operable to receive the train of pulses;

one or more signal processors, operable to communicate with the receivers to identify the body pulses received in the train of pulses above a predetermined body pulse strength threshold value and to associate the body pulses received in the train of pulses above a predetermined body pulse strength threshold value with a range value.

In an exemplary embodiment, there is provided a system for range finding between a signal transmitter and a signal receiver comprising:

a plurality of signal transmitters, each operable to transmit a ranging signal having a corresponding train of pulses forming a data stream representing a ranging message including a series of preamble pulses having a common carrier frequency and a relatively constant pulse strength, the series of preamble pulses having a pattern corresponding to a predetermined preamble segment of the message, each preamble segment including data representative of an identity of the corresponding signal transmitter, the data stream including a series of body pulses representative of a body segment of the message, the body pulses having a common carrier frequency with the preamble pulses, each of the body pulses having a pulse strength, the pulse strength varying across the series of body pulses in a predetermined pulse strength pattern, one or more signal receivers to be located at or near the remote location, the receiver operable to receive the train of pulses;

one or more signal processors, operable to communicate with the receivers to identify the body pulses received in the train of pulses above a predetermined body pulse strength threshold value and to associate the body pulses received in the train of pulses above a predetermined body pulse strength threshold value with a range value.

In an exemplary embodiment, there is provided a system as defined, the one or more signal processors operable to count the body pulses received in the train of pulses above the predetermined body pulse strength threshold value, the count value being representative of the range value.

In an exemplary embodiment, there is provided a system as defined the signal transmitters including a first signal transmitter, the one or more receivers including a first receiver located proximal to the first signal transmitter and a second receiver located distal to the first signal transmitter, the first receiver achieving a higher count value than the second receiver.

In an exemplary embodiment, there is provided a system as defined, the signal transmitters including a first signal transmitter, the one or more receivers including a first receiver to generate a first count value, the first receiver count value being reduced with increasing distance between the first signal transmitter and the first receiver.

In an exemplary embodiment, there is provided a system as defined, the signal transmitters includes a first transmitter and a second transmitter, each configured to transmit respective first and second ranging signals, each including a unique preamble segment, the one or more signal receivers including a first receiver and a second receiver at least one of signal processors being operable to communicate with the first receiver to associate the body pulses received in the train of pulses from the first transmitter above a predetermined body pulse strength threshold value with a first range value, the second signal processor operable to communicate with the second receiver to associate the body pulses received in the train of pulses from the second transmitter above a predetermined body pulse strength threshold value with a second range value.

In an exemplary embodiment, there is provided a system as defined, the signal processors including a first signal processor communicating with the first receiver and a second signal processor communicating with the second processor.

In an exemplary embodiment, there is provided a system as defined, further comprising at least one reflective surface between the signal transmitters and signal receivers and, for each signal receiver, the corresponding range value relating to the distance between the signal transmitter and the reflective surface added to the distance between the reflective surface and the receiver.

In an exemplary embodiment, there is provided a method of finding range between a source location and a remote location, comprising:
  issuing, from the source location, a train of pulses forming a data stream representing a message and including a series of preamble pulses having a common carrier frequency and a relatively constant pulse strength, the series of preamble pulses having a pattern corresponding to a predetermined preamble segment of the message, the data stream including a series of body pulses representative of a body segment of the message, the body pulses having a common carrier frequency with the preamble pulses, each of the body pulses having a pulse strength, the pulse strength varying across the series of body pulses in a predetermined pulse strength pattern,
  receiving, at the remote location, the train of pulses;
  identifying the body pulses received in the train of pulses above a predetermined body pulse strength threshold value; and
  associating the train of pulses above a predetermined body pulse strength threshold value with a range value between the source and remote locations.

In an exemplary embodiment, there is provided a method of finding range between a plurality of source locations and a plurality of remote locations, comprising:
  issuing, from each source location, a ranging signal including a train of pulses forming a data stream representing a ranging message and including a series of preamble pulses, the preamble pulses having a common carrier frequency and a relatively constant pulse strength, the series of preamble pulses having a pattern corresponding to a predetermined preamble segment of the message and unique to the source location, the data stream including a series of body pulses representative of a body segment of the message, the body pulses having a common carrier frequency with the header pulses, each of the body pulses having a pulse strength, the pulse strength varying across the series of body pulses in a predetermined pulse strength pattern;
  receiving the ranging signal at each remote location;
  identifying, in each ranging signal, the body pulses received in the train of pulses above a predetermined body pulse strength threshold value; and
  associating, for reach ranging signal, the train of pulses above a predetermined body pulse strength threshold value with a range value between the respective source and remote locations.

In an exemplary embodiment, there is provided a system for sensing position, comprising a transmitter operable to transmit a signal including a train of pulses with varying pulse strength along the train to form a pulse pattern, a plurality of receivers in spaced relation relative to the transmitter and one another, each receiver operable to receive the signal with a different version of the pulse pattern according to the position of the receiver relative to the transmitter; and an electronic circuit coupled to the receiver and operable to determine a location of the transmitter, based on a comparison of the corresponding versions of the pulse pattern received by each receiver.

In an exemplary embodiment, there is provided a system as defined, further comprising at least one additional transmitter, each of the transmitters operable to transmit a signal having a unique identity, the electronic circuit further operable to distinguish each of the transmitters from the other based on the unique identity, the electronic circuit being further operable to determine a location of each of the transmitting devices substantially simultaneously.

In an exemplary embodiment, there is provided a system as defined, each receiver including a wave energy input device which is spaced from each of the wave energy input devices of the other receivers at a distance independent of the wavelength of the signal.

In an exemplary embodiment, there is provided a system as defined, the signals being based on a predetermined pulse strength coding scheme and/or a predetermined pulse-coding scheme.

In an exemplary embodiment, there is provided a system as defined, the signals including one or more groups of pulses.

In an exemplary embodiment, there is provided a system as defined, the unique identity including one or more unique data field code-words assigned to each transmitter.

In an exemplary embodiment, there is provided a system as defined, wherein the signals are identifiable by at least one preamble or data field identity code, operational data field, time-synchronizing data code, and/or ranging code.

In an exemplary embodiment, there is provided a system as defined, the signal including a signal ranging code, wherein the different versions of the pulse pattern are identifiable using variable radiated signal strength that is varied in a sequence which includes the actual data code.

In an exemplary embodiment, there is provided a system as defined, wherein the transmitter is affixed to a pointing device and the electronic circuit is coupled with an input device operatively associated with a personal computer having a display device and such that the pointing device is operable to move a cursor on the display device.

In an exemplary embodiment, there is provided a system as defined, wherein the pointing device includes at least one button for user actuation and the signals are based on what is available directly, coded into, and/or modulated in the preamble.

In an exemplary embodiment, there is provided a system as defined, the transmitter device including a power supply including at least one battery, solar cell, and/or coil.

In an exemplary embodiment, there is provided a system as defined, the coil being operable to receive energy from an EM powering field radiating proximal to the power supply.

In an exemplary embodiment, there is provided a system as defined, the coil operable to induce electrical energy from a magnetic field by mechanical motion.

In an exemplary embodiment, The system comprising two receivers and the location is expressed as a range and a variation in a single-dimension.

In an exemplary embodiment, there is provided a system wherein at least one of the transmitters and at least one of the receivers remain fixed during operation for the purpose of self calibrating.

In an exemplary embodiment, there is provided a system comprising at least three of the receivers arranged in a first triangular grouping and at least three receivers grouped in a second grouping, the electronic circuit being operable to receive a first input from the first grouping and further operable to receive a second input from a second grouping, the groupings having only one of the receivers in common, the electronic circuit further operable to determine a range and at least two dimensional position of the transmitter based on a comparison of the first input and the second input.

In an exemplary embodiment, there is provided a system comprising at least four receiver units arranged in a rectangular format, the electronic circuit operable to receive four separate inputs from four respective pairings of two receivers each, the electronic circuit further operable to determine a three dimensional position of the transmitting device based on a comparison of the separate inputs.

In an exemplary embodiment, there is provided a system, wherein the rectangular format is a plane arranged around a periphery of a computer display.

In an exemplary embodiment, there is provided a system, comprising at least eight receiver units arranged in a cube, the electronic circuit operable to receive eight separate inputs from eight respective pairings of the eight receiver units in groups of two, the electronic circuit further operable to determine a three dimensional position of the transmitting device in relation to the cube based on a comparison of the separate inputs.

In an exemplary embodiment, there is provided a system, the electronic circuit including at least a multichannel channel processor connected to the receivers, a detector and a position calculator connected to the multiple channel processor, and an output device for presenting the location to an electronic peripheral attachable to the output device.

In an exemplary embodiment, there is provided a system, the electronic peripheral being a general purpose computer and a display device, the general purpose computer being configured to present a representation of the location on the display device.

In an exemplary embodiment, there is provided a system, the multiple channel processor including a digital signal receiver coupled to the receiver unit to receive input therefrom, the channel processor further comprising a detector, a band-pass filter, an automatic gain controller, and/or a threshold programmable comparator; the channel processor further comprising a signal strength data calculator for determining pulse count information from the received digital signals and for outputting the pulse count information In an exemplary embodiment, there is provided a system, the signal including a signal strength code for receiving the amplitude information, a transmitter detector code for determining an identity of the transmitting device, a data signal extractor code for determining any specific data embedded in the radio signal respective to the transmitting device.

In an exemplary embodiment, there is provided a system, the transmitter including a power supply, a signal strength code generator, a carrier code generator interconnected by a signal modulator; the transmitter device further comprising a pulse shaping module for shaping a waveform output from the signal modulator; the transmitter device further comprising a wave emitter connected to an output of the pulse shaping modulator for outputting the signal.

In an exemplary embodiment, there is provided a system, the wave emitter including an infra-red or light emitting diode, a laser emitter, a radio antenna and/or a piezo-coupler.

In an exemplary embodiment, there is provided a system, the signal code generator being coupled to a microprocessor.

In an exemplary embodiment, there is provided a system, the signal code generator further comprising a switch for selectively changing the signal strength code to another code when the switch is activated.

In an exemplary embodiment, there is provided a system wherein the transmitter device is incorporated into a computer interface including a mouse, a tilt-joystick, a pointer controller, a six-degree-of-freedom interface, or a gesture interface.

In an exemplary embodiment, there is provided a system wherein, the transmitter is incorporated into a surgical instrument.

In an exemplary embodiment, there is provided a system wherein the transmitter is incorporated into an industrial robot, a golf mat, or speed measurement device.

In an exemplary embodiment, there is provided a system, wherein each receiver includes a wave energy input device and a receiver element.

In an exemplary embodiment, there is provided a system, the wave energy input device including a diode, antenna, or piezo-coupler.

In an exemplary embodiment, there is provided a system, wherein the receiver element comprises a low-noise amplifier connected to the wave energy input device, a band-pass filter connected to the low-noise amplifier, and an automatic gain controller circuit connected to the band-pass filter for outputting to the electronic circuit, and feeding back to the low-noise amplifier, and a programmable threshold comparator, output to a pulse counting processor.

In an exemplary embodiment, there is provided a transmitting device operable to transmit a signal, the transmitter for communication with one or more receiver units in spaced relation to the transmitter and an electronic circuit connected to at least one receiver to receive a radio signal in order to determine a range of the transmitting device according to a variation in signal strength of the radio signal over a predetermined sensing time period.

In an exemplary embodiment, there is provided a receiver unit operable to receive a signal transmitted from a transmitting device; the receiver unit for placement in spaced relation to another substantially identical receiver unit such that each receiver unit is operable to receive a different version of the signal, the receiver unit for connection to an electronic circuit connectable to both of the receiver units, the electronic circuit being operable to determine a location of the signal transmitting device in relation to the receiver units based on a comparison between each the different version of the signal.

In an exemplary embodiment, there is provided a method for sensing position comprising receiving a first signal from a first transmitting device, the version including a body segment therein with a first version of a train of pulses; receiving a second signal from the first transmitting device, the second segment including the body segment with a second version of the train of pulses; and determining a location of the transmitting device based on a comparison of the first version and the second version.

In an exemplary embodiment, there is provided a method further comprising the steps of receiving a first signal from a second transmitting device, the first signal including a body segment with a first version of a train of pulses, the second signal being sent at a different time to the first signal; receiving a second signal from the second transmitting device, the second signal including a body segment having a second version of the train of pulses; determining a range and/or location of the first transmitting device based on a comparison of the first and second versions of second signal.

In an exemplary embodiment, there is provided a method, the receiving steps including providing a wave energy input device to receive the signal and an additional wave energy input device to receive the additional signal, the wave energy input devices being spaced apart at a fixed distance independent to the wavelength of the signal and the additional signal.

In an exemplary embodiment, there is provided a method, wherein the signal and additional signal are based on a code and signal strength variable algorithm.

In an exemplary embodiment, there is provided a method, wherein the simultaneous pulse code and signal strength variable algorithm include an incrementally ramped sequence, a decrementally ramped sequence, and/or a randomly selected strength code.

In an exemplary embodiment, there is provided a method, the algorithm based on a code allowing for a unique signal strength pattern of the signal to be identified and a unique range to be calculated.

In an exemplary embodiment, there is provided a method, wherein different versions of the signal are identifiable via a different pulsed code that are unique code-words assigned to each of the transmitting devices.

In an exemplary embodiment, there is provided a method wherein the signal is a radio signal, and the different versions of the signal are identifiable via a different signal strength code and between the versions.

In an exemplary embodiment, there is provided a method wherein the different versions of the radio signal are identifiable using at least one of a radiated signal strength coding technique and a pulse-coding technique.

In an exemplary embodiment, there is provided a method, further comprising the steps of providing the transmitting device on a pointing device and providing the electronic circuit in a coupling with an input device on a personal computer having a display device and such that the pointing device is operable to move a cursor on the display device.

In an exemplary embodiment, there is provided a method, wherein the pointing device includes at least one button for user actuation and the signal is based on data formatted in the preamble or ranging codeword, and wherein an actuation of the button is transmitted to the receiver units via altering the codeword for at least one ranging period.

In an exemplary embodiment, there is provided a method wherein a power supply incorporated into the transmitting device is selected from the group including a battery, a solar cell, a coil operable to receive energy from an EM powering field radiating proximal to the power supply, or a coil operable to induce electrical energy from a magnetic field by mechanical motion.

In an exemplary embodiment, there is provided a method the unique identity of different transmitting devices is effected through unique data field codes in each transmitting device.

In an exemplary embodiment, there is provided a system for sensing position comprising at least two transmitting devices each operable to transmit a unique radio signal; at least two receiver units—in spaced relation to each other and each operable to receive a different version of each signals, the receiver units comprising a wave energy input device and a receiver element; and, an electronic circuit coupled to the receiver element and operable to substantially simultaneously determine a location of each of the transmitting devices in relation to the receiver units by distinguishing the transmitting devices based on the unique data field and based on a comparison between each the different version of each respective signal.

In an exemplary embodiment, there is provided a system wherein the wave energy input device associated with each of the receiver units are spaced apart at a distance independent of the wavelength of the radio signal.

In an exemplary embodiment, there is provided a system wherein the signals include unique data field code-words assigned to each of the transmitting devices.

In an exemplary embodiment, there is provided a system wherein the different versions of the signal are identifiable using at least one of a radiated signal strength technique and a pulse-coding technique.

In an exemplary embodiment, there is provided a transmitting system for identifying and locating one or more transmitting devices in a transmitting area, comprising at least one transmitting means for transmitting a signal on a propagating medium throughout the transmitting area and coupling the signal to the propagating medium, the transmitting signal comprising a combined pulsed coding component and a signal strength coding component; each transmitted signal including a unique code identifying the respective device; signal receiving means associated with the transmitting area and connected to the propagating medium to receive at least one transmitting signal from the one or more transmitting devices; means for decoding the transmitting signal to identify at least one of the transmitting devices, and further including means for determining the position of at least one of the transmitting devices in the transmitting range.

In an exemplary embodiment, there is provided a transmitting system, wherein the one or more transmitting devices are active devices.

In an exemplary embodiment, there is provided a transmitting system, further including means for generating an energy field in the propagating medium within the transmitting range.

In an exemplary embodiment, there is provided a transmitting system, wherein, the energy field includes a signal strength varying component.

In an exemplary embodiment, there is provided a transmitting-system, wherein each of the transmitting devices includes a means to receive a signal through the energy field for active transmitting device operation.

In an exemplary embodiment, there is provided a transmitting system, wherein the energy field includes an EM field, a visible light energy field, a magnetic field, or an acoustic field.

In an exemplary embodiment, there is provided a transmitting system, wherein the propagating medium comprises free space in the transmitting range.

In an exemplary embodiment, there is provided a transmitting system, wherein the propagating medium comprises an occlusion in the transmitting range.

In an exemplary embodiment, there is provided a transmitting system, wherein the signal-strength variation and pulse coding represents a unique strength level coding and/or range coding.

In an exemplary embodiment, there is provided a transmitting system, wherein the signal strength coding is a forward-ramped or reverse ramped code.

In an exemplary embodiment, there is provided a transmitting system, wherein the pulsed-coding signal component modulation is Amplitude Shift Keying (ASK).

In an exemplary embodiment, there is provided a transmitting system, wherein the pulsed-coding signal component modulation is Frequency Shift Keying (FSK).

In an exemplary embodiment, there is provided a transmitting system, wherein the unique codes of the one or more transmitting devices are in the data field.

In an exemplary embodiment, there is provided a transmitting system, wherein the one or more transmitting devices are active devices that generate a transmitting signal.

In an exemplary embodiment, there is provided a transmitting system, wherein the transmitting signal is an electromagnetic signal.

In an exemplary embodiment, there is provided a transmitting system, wherein the propagating medium comprises an EM reflecting and conducting layer in the transmitting range.

In an exemplary embodiment, there is provided a transmitting system, wherein the signal receiver means includes a plurality of spaced-apart signal receivers; and the means for determining the position of each of the one or more transmitting devices includes means for calculating the received signal strengths of the radio transmitting signals passing through the propagating medium to the plurality of signal receivers.

In an exemplary embodiment, there is provided a transmitting system, wherein the means for decoding and identifying each of the one or more transmitting devices includes a means for comparing and filtering-out received transmitting signals to stored identifying codes of the one or more transmitting devices.

In an exemplary embodiment, there is provided a transmitting system for identifying and locating one or more transmitting devices in a transmitting range, including: a signal propagating medium for conducting signals throughout the transmitting area; at least one of the transmitting devices including means for producing a transmitting signal and coupling the signal to the propagating medium; the transmitting signal comprising a signal strength coding and/or a pulse coding; each transmitting signal including a unique code identifying the respective transmitting device; signal receiving means associated with the transmitting area and connected to the propagating medium to receive at least one transmitting signals from the one or more transmitting devices; a means for decoding the transmitting signals to identify the one or more transmitting devices; and, means for determining the position of the one or more transmitting devices in the transmitting range.

In an exemplary embodiment, there is provided a transmitting system, wherein a portion of the one or more transmitting devices are active devices that generate a transmitting signal, and another portion of the one or more transmitting devices are active transceiver devices.

In an exemplary embodiment, there is provided a system for sensing a location of at least two transmitters, said system comprising at least two transmitters, each transmitter being operable to transmit a unique signal, at least two receivers in spaced relation to one another and to said transmitters, said at least two receivers each being operable to receive a different version of each of said signals, said receivers having a wave energy input device and a receiving element, and electronic circuit being coupled to said receiving element and being operable to substantially simultaneously determine a location of each of said transmitters in relation to said receivers by distinguishing said transmitters based on a unique data field, and based on a comparison between each of said different versions of each signal.

In an exemplary embodiment, there is provided a system for sensing a location of a transmitter, said transmitter being construed to emit a peculiar signal, said receiver being operable to receive said peculiar signal and to identify said transmitter based on said peculiar signal, an electric circuit coupled to said receiver and being operable to determine a location of said transmitter in relation to said receiver based on properties of said signal.

In an exemplary embodiment, there is provided a system for sensing position comprising: (a) a transmitter operable to transmit a pulsed wave oriented signal with a signal strength variation; (b) at least one receiver placed in spaced relation between said transmitter and said receiver; (c) said transmitter simultaneously sending a timed burst pattern and a power burst pattern; (d) at least one additional receiver, each receiver being operable to receive a different version of said signal; and (e) an electronic circuit coupled to said receivers and operable to determine a position of said transmitter in relation to said receivers based on a comparison between each version of said signal.

In an exemplary embodiment, there is provided a system as claimed in, wherein there is at least one additional transmitter, each of the transmitters being operable to transmit a signal with an identity and a signal strength variation: (a) said electronic circuit being further operable to distinguish each of the transmitters from the other transmitters based on a received identity signal strength variation; and (b) said electronic circuit being operable to determine a location of said transmitters substantially simultaneously.

In an exemplary embodiment, there is provided a system for sensing a position comprising a plurality of transmitters, each transmitter being operable to transmit a pulsed wave oriented signal that is sent simultaneously as a timed burst pattern and a power burst pattern, the signal from each transmitter being distinguishable from said signals of each of the other transmitters, there being a plurality of receivers, each receiver being operable to receive a different version of said signals from said transmitters, an electronic circuit coupled to said receivers and being operable to determine a location of each of the said transmitters in relation to said receivers based on a comparison between different versions of said signals.

In an exemplary embodiment, there is provided a system for detecting a range value between two locations, comprising a transmitter associated with a first location and a receiver associated with a second location, the transmitter operable to emit a train of pulses arranged in identifiable groups, each group including a number of pulses that vary in discreet values of signal strength, the receiver being operable between an inactive condition and an active condition, if the strength is greater than a known threshold, and not active otherwise.

In an exemplary embodiment, there is provided a system for detecting a range value between two locations, comprising a transmitter associated with a first location and a receiver associated with a second location, the transmitter operable to emit a train of pulses arranged in identifiable groups, each group including a number of pulses that vary in discreet values of signal strength, the receiver being operable between an inactive condition and an active condition, if the strength is greater than a known threshold, and not active otherwise.

In an exemplary embodiment, there is provided a method for detecting a range value between two locations, comprising transmitting, at a first location, a train of pulses arranged in identifiable groups, each group including a number of pulses that vary in discreet values of signal strength, receiving the train of pulses at a second location, determining a minimum strength in the train of pulses, activating a detecting condition when the minimum strength exceeds a predetermined threshold.

In an exemplary embodiment, there is provided a method of determining a relative position of a first location relative to a second location, comprising emitting a signal from one of the locations, the signal carrying a sequence of pulses that vary in range as a set of discreet values of signal strength, receiving the signal from the other of the locations, measuring a minimum signal strength value from the signal and associating the minimum strength value with a corresponding relative position.

In an exemplary embodiment, there is provided a method as defined, further comprising providing a predetermined threshold for the minimum strength value, and adjusting the predetermined threshold.

In an exemplary embodiment, there is provided a method as defined, the step of associating including accessing a lookup table for a correlation between the minimum strength value and the corresponding relative position.

In an exemplary embodiment, there is provided a method as defined, the step of associating including accessing a predetermined converter function for each minimum strength value to generate a corresponding relative position value.

In an exemplary embodiment, there is provided a method as defined, further comprising the step of generating a signal waveform including a ranging segment waveform, according to a power function, $R(x)$ as an increasing and/or decreasing, nonlinear and/or linear range-code, or an algorithm carrying out one or more subroutines to select or identify elements of the ranging segment waveform.

In an exemplary embodiment, there is provided a method further comprising the step of generating a signal waveform including a ranging segment waveform, according to an algorithm carrying out one or more subroutines to select, identify, or quantify according to one or more power functions, elements of the ranging segment waveform.

The above-described embodiments of the invention are intended to be examples of the present invention and alterations and modifications may be effected thereto, by those of skill in the art, without departing from the scope of the invention which is defined solely by the claims appended hereto.

I claim:

1. A device configured to convey a signal for determining a distance travelled by the signal between the device and a receiver, the device comprising a transmitter configured to transmit a series of pulses having a varying pulse strength that varies across the series of pulses in accordance with a designated pulse strength profile, wherein the series of pulses comprises a series of body pulses, and wherein the transmitter is configured to transmit a train of pulses including a series of preamble pulses having a substantially constant pulse strength, and the series of body pulses, and a signal processor configured to process the body pulses received by the receiver, and to output a value according to a number of said body pulses above a designated threshold value, representative of the distance travelled.

2. The device as defined in claim 1, wherein the pulse strength profile comprises at least one of (i) a progressively increasing pulse strength pattern, and (ii) a progressively decreasing pulse strength pattern.

3. The device as defined in claim 1, wherein the pulse strength profile comprises at least one of (i) a fixed pulse strength pattern of said varying pulse strengths, (ii) a random pulse strength pattern of said varying pulse strengths, and (iii) a varying pulse strength pattern of said varying pulse strengths.

4. The device as defined in claim 1, wherein a carrier frequency of the transmitter is selected from the group comprising: near infrared, far infrared, visible, ultra-violet, high frequency radio, and ultrasonic.

5. The device as defined in claim 1, further comprising a processor configured to control generation of a signal waveform to be applied to the series of pulses in defining said designated pulse strength profile according to a power function $R(x)$, where x is a pulse number which increases from zero to N, and where $R(x)$ is a power level calculated as a function of the pulse number x to vary between a power level of zero and a maximum power level of N.

6. The device as defined in claim 5, wherein said power function is selected from an incrementing function $R(x)=x$, and a decrementing function $R(x)=N-x$.

7. The device as defined in claim 5, wherein said power function defines an interleaved pattern.

8. The device as defined in claim 1, wherein the preamble pulses define at least one of a unique transmitter identifier and a synchronization code.

9. The device as defined in claim 1, wherein the train of pulses forms a data stream representing a message including the series of preamble pulses having a common carrier frequency, the series of preamble pulses having a pattern corresponding to a predetermined preamble segment of the message, the data stream further including the series of body pulses representative of a body segment of the message, the body pulses including a common carrier frequency with the preamble pulses.

10. The device as defined in claim 1, wherein the device is incorporated into a computer interface selected from the group comprising a mouse, a tilt-joystick, a pointer controller, a six-degree-of-freedom interface, and a gesture interface.

11. A system comprising:
a transmitter configured to transmit a signal formed at least in part by a train of pulses including a series of preamble pulses having a substantially constant pulse strength, and a series of body pulses having a pulse strength that varies across said series of body pulses in accordance with a designated pulse strength profile;
a receiver to receive at least a subset of the series of body pulses above a designated threshold value; and
a signal processor operatively coupled to said receiver, said signal processor configured to output a range value according to a number of said body pulses above the designated threshold value, the range value representative of a distance travelled by the train of pulses between said transmitter and said receiver.

12. The system as defined in claim 11, wherein said series of pulses is reflected off an object, the range value representative of a distance travelled by said series between the transmitter, the object, and the receiver.

13. The system as defined in claim 11, further comprising two or more emitters each configured to transmit a respective series of said body pulses, and a respective series of preamble pulses encoding an identifier associated therewith, said signal processor identifying a source of the received pulses from each said associated identifier to output a respective range value for each of said emitters.

14. The system as defined in claim 13, wherein each of said emitters operates from a common transmitting device, said emitters on said transmitting device configured to communicate with said signal processor, the signal processor thereby configured to track, at least in part, at least one of a position and an orientation of the transmitting device from each said respective range value.

15. The system as defined in claim 11, further comprising two or more receivers, said signal processor operatively coupled to each of said receivers and configured to synchronize processing of said received body pulses from each of said receivers to output a respective range value representative of a respective distance travelled by said series of pulses between said transmitter and each of said receivers.

16. A signal processor configured to operatively couple to one or more receivers for processing a transmitted signal received thereby to identify a distance travelled by the transmitted signal, the transmitted signal comprising a train of pulses including a series of body pulses having a transmitted pulse strength that varies across the series in accordance with a designated pulse strength profile, and a series of preamble pulses having a substantially constant pulse strength and encoding a transmitter identifier, the signal processor configured to output a range value according to a number of said body pulses above a designated threshold value, the range value representative of the distance travelled by the transmitted signal.

17. The signal processor as defined in claim 16, wherein the signal processor is further configured to:
    identify a signal transmitter for each of a plurality of transmitted signals;
    associate a respective range value for each of the transmitted signals; and
    calculate, at least in part, at least one of a relative position and orientation of each of said transmitters from each said respective range value.

18. The signal processor as defined in claim 16, wherein the transmitted signal is emitted by a transmitter and received concurrently by two or more receivers, the signal processor being further configured to:
    access a synchronization code received in association with the transmitted signal by each of the two or more receivers;
    synchronize processing of the concurrently received signals via said synchronization code to output respective range values representative of a distance travelled by the signal to each of said two or more receivers; and
    calculate, at least in part, at least one of a position and an orientation of the transmitter as a function of said respective range values.

19. The signal processor as defined in claim 16, the distance travelled comprising a distance travelled by the transmitted signal from a designated transmitter to a reflective object and from the reflective object to the one or more receivers, the signal processor configured to:
    access a designated location of the one or more receivers relative to the designated transmitter; and
    calculate, at least in part, at least one of a position and an orientation of the reflective object relative to the one or more receivers and designated transmitter based on said range value and said designated location.

20. A method for identifying a distance travelled by a signal between an emitter and a receiver, comprising:
    generating a signal formed at least in part by a series of pulses having a pulse strength that varies across said series in accordance with a designated transmission pulse strength profile;
    transmitting said signal via the emitter;
    receiving, at the receiver, at least a subset of said series of pulses with a pulse strength profile and above a designated pulse strength threshold;
    implementing a count associated with the subset of received pulses above the designated pulse strength threshold,
    correlating the count with a distance travelled by the signal between the emitter and the receiver.

21. The method as defined in claim 20, wherein said implementing comprises associating a pre-calibrated range value with said count, the range value being representative of said distance.

22. The method as defined in claim 20, wherein said pulse strength profile comprises a patterned pulse strength profile selected from a progressively increasing pattern and a progressively decreasing pattern.

23. The method as defined in claim 20, further comprising:
    receiving a respective subset of said series of pulses at each of the receivers;
    synchronizing detection of said received pulse strength profile for each of said receivers; and
    correlating each said detected pulse strength profile with a respective distance.

24. The method as defined in claim 20, for identifying a distance travelled by the signal from two or more emitters, the method further comprising:
    transmitting said signal from each of the emitters along with an respective identification code;
    receiving each said respective identification code and a corresponding subset of said series of pulses at the receiver from each of the emitters;
    detecting a respective received pulse strength profile for each of said emitters; and
    correlating each said detected pulse strength profile with a respective distance.

25. The method as defined in claim 20, wherein the transmitted signal travels from the emitter to the receiver via a reflective object, the method further comprising determining, at least in part, at least one of a position and an orientation of the reflective object as a function of said distance.

* * * * *